US012616754B2

(12) United States Patent (10) Patent No.: US 12,616,754 B2

Jan et al. (45) Date of Patent: May 5, 2026

(54) COMPOSITION FOR DELIVERY OF A BIOACTIVE AGENT AND METHOD OF MANUFACTURE AND USE THEREOF

(71) Applicant: NATIONAL CHENG KUNG UNIVERSITY, Tainan (TW)

(72) Inventors: Jeng-Shiung Jan, Tainan (TW); Yu-Fon Chen, Tainan (TW)

(73) Assignee: NATIONAL CHENG KUNG UNIVERSITY, Tainan City (TW)

( * ) Notice: Subject to any disclaimer, the term of this patent is extended or adjusted under 35 U.S.C. 154(b) by 808 days.

(21) Appl. No.: 17/907,011

(22) PCT Filed: Jul. 14, 2020

(86) PCT No.: PCT/CN2020/101931

§ 371 (c)(1),
(2) Date: Sep. 22, 2022

(87) PCT Pub. No.: WO2022/011559

PCT Pub. Date: Jan. 20, 2022

(65) Prior Publication Data

US 2023/0143135 A1 May 11, 2023

(51) Int. Cl.

| A61K 47/61 | (2017.01) |
| A61K 36/185 | (2006.01) |
| A61K 36/752 | (2006.01) |
| A61K 39/108 | (2006.01) |
| A61K 39/145 | (2006.01) |
| A61K 39/385 | (2006.01) |

(Continued)

(52) U.S. Cl.
CPC ............ *A61K 47/61* (2017.08); *A61K 36/185* (2013.01); *A61K 36/752* (2013.01); *A61K 39/0258* (2013.01); *A61K 39/145* (2013.01); *A61K 39/385* (2013.01); *A61K 47/545* (2017.08); *A61K 2039/6025* (2013.01)

(58) Field of Classification Search
CPC .................. A61K 27/61; A61K 36/165; A61K 2039/6025; A61K 47/61; Y02A 50/30
See application file for complete search history.

(56) References Cited

U.S. PATENT DOCUMENTS

| 2011/0052697 A1 | 3/2011 | Farokhzad |
| 2014/0335184 A1 | 11/2014 | Park |

FOREIGN PATENT DOCUMENTS

| CN | 103976941 A | 8/2014 |
| CN | 107281497 A | 10/2017 |
| KR | 20140094697 A | 7/2014 |

OTHER PUBLICATIONS

Chen et al, Naturally Derived DNA Nanogels as Ph and Glutathione Triggered Anti-Cancer Drug Carrier, Materials Science and Engineering C, vol. 114, pp. 1-9. (Year: 2020).*

(Continued)

*Primary Examiner* — Carlos A Azpuru
(74) *Attorney, Agent, or Firm* — HSML P.C.

(57) ABSTRACT

Provided is a composition and method for delivery of bioactive agents to a cell or a subject. The composition includes nucleic acids derived from plants and the bioactive agents, and the nucleic acids are crossed linked by a cross-linking agent. Such composition is non-toxic, biocompatible and target specific. A method of making the composition is also provided.

18 Claims, 27 Drawing Sheets

(51) Int. Cl.
  *A61K 47/54*        (2017.01)
  *A61K 39/00*        (2006.01)

(56)                References Cited

OTHER PUBLICATIONS

Chen et al, Derived Nanogels as pH and Glutathione Triggered Anti-Cancer Drug Carrier, Materials Science and Engineering C, vol. 114, pp. 1-19. (Year: 2020).*

International Search Report and Written Opinion issued in PCT/CN2020/101931, mailed Apr. 16, 2021.

Chen, Yu-Fon et al., "Naturally derived DNA nanogels as pH- and glutathione-triggered anticancer drug carriers", Materials Science & Engineering C, vol. 114, May 1, 2020, pp. 1-9; cited in ISR.

Liu, Juan et al., "Multifunctional aptamer-based nanoparticles for targeted drug delivery to circumvent cancer resistance", Biomaterials, vol. 91, Mar. 10, 2016, pp. 44-56, cited in ISR.

* cited by examiner 1.25 µg/mL          2.5 µg/mL

DNA

Free DOX

DNA-DOX
NGs (genipin)

DNA-DOX
NGs (DTSSP)

Blank

Fig.7A

| | Free-DOX | | | | DNA-DOX NGs (DTSSP) | | |
|---|---|---|---|---|---|---|---|
| DNA (µg/mL) | 10 | - | - | - | 2.5 | 5 | 10 |
| DOX (µg/mL) | - | 1 | 2.5 | 5 | 1 | 2.5 | 5 |

| | Free-DOX | | | | DNA-DOX NGs (DTSSP) | | |
|---|---|---|---|---|---|---|---|
| DNA (µg/mL) | 10 | – | – | – | 2.5 | 5 | 10 |
| DOX (µg/mL) | – | 1 | 2.5 | 5 | 1 | 2.5 | 5 |

COMPOSITION FOR DELIVERY OF A BIOACTIVE AGENT AND METHOD OF MANUFACTURE AND USE THEREOF

BACKGROUND

1. Technical Field

The present disclosure relates to compositions comprising nucleic acids as biomaterials to deliver bioactive agents, and more specifically to the use of naturally derived nucleic acids for drug delivery. The present disclosure also relates to methods of manufacture and use of the compositions comprising nucleic acids as drug delivery biomaterials.

2. Description of Related Art

Cancers remain the major threats to human health. Among the various approach to treat cancer, chemotherapy is one of the most adopted treatment. Conventional chemotherapy causes cancer cells to stop growth and division by interfering with their DNA replication and cell mitosis. However, these agents are non-specific when being delivered into a subject for cancer treatment and could also harm healthy tissues, leading to unintended side effects. These side effects could be so severe that the damage made on healthy tissues has been related to a high mortality rate of cancer patients. Furthermore, the efficiency of delivering chemotherapeutic drugs to malignant tumors is relatively poor and requires high doses to be effective, further exacerbating damage of healthy tissues and inducing multidrug resistance. Therefore, the development of treatments that are specific toward cancer cells and have less side effects and higher therapeutic efficacy is of high priority in cancer treatment.

In recent years, a range of bioavailable materials have emerged as candidates to improve therapeutic efficacies. These include polymeric nanoparticles, hydrogels, liposomes, and inorganic carriers that are designed to be activated under certain conditions. For example, the bioavailable material can be activated and release the active agent based on the characteristics of cancer cells such as pH differences, oxygen requirements, redox potentials, reactive oxygen species (ROS) and enzymes when being delivered into tumor's microenvironment. However, the availability of such biomaterials and cost-effectiveness of manufacture thereof into an adequate carrier for delivery of bioactive agents remain as the challenges in the field. For example, using DNA-origami to design nanocarriers has been a promising strategy for drug delivery, and nanostructures have been designed in rational geometries and precise spatial addressability, relying on the hydrogen bonding of complementary nitrogenous bases to maintain their structures. However, these approaches often lead to less than 100% yield of the desired product due to mis-assembly or misfolding, and their preparation is often very expensive.

Thus, a non-toxic and effective delivery of a bioactive agent is still in need for safe and efficient treatment of cancers and other diseases.

SUMMARY

Herein, the present disclosure is therefore provided with a composition and a method of manufacture thereof for delivering a bioactive agent to a subject in need thereof.

In an aspect, the present disclosure provides a composition comprising a plant-derived nucleic acid and a bioactive agent, wherein the plant-derived nucleic acid is crosslinked with a cross-linking agent. In one embodiment, the composition comprises a plant-derived nucleic acid that is derived from a soft part of a plant, e.g., fruits, leaves, petals, flowers, roots or stems of a plant. In another embodiment, the nucleic acid is derived from a seed of the fruit of the plant. In a further embodiment, the fruit from which the nucleic acid is derived is kiwifruit, dragon fruit, pineapple, papaya, apple, lemon, orange, tangerine, tomato, mango, litchi, pear, date, passion fruit, banana, sweet potato, corn or a combination thereof.

In an embodiment, the composition comprises a plant-derived nucleic acid with GC content greater than 40%. In another embodiment, the plant-derived nucleic acid has a GC content greater than 30%, 35%, 36%, 37%, 38%, 39%, 40%, 41%, 42%, 43%, 44%, 45%, 46%, 47%, 48%, 49%, 50%, or 55%.

In an embodiment, the composition comprising a plant-derived nucleic acid and a bioactive agent, wherein the plant-derived nucleic acid is crosslinked with a cross-linking agent that cross-links primary amines or hydroxyl groups of the nucleic acid. In another embodiment, the cross-linking agent is genipin, 3,3'-dithiobis (sulfosuccinimidyl propionate), citric acid, transglutaminase, glutaraldehyde, 1,4-butanediol diglycidyl ether, carbodiimide, tannic acid, sulfonate, oxidized dextrins, hydrazide, alkoxyamine, ketone, periodic acid, calcium chloride, calcium carbonate or a combination thereof.

In an embodiment, the composition has a hydrodynamic diameter of from 50 nm to 5 μm. In another embodiment, the composition has a hydrodynamic diameter in a range of from 100 nm to 1 μm. In a further embodiment, the composition has a hydrodynamic diameter in a range of from 100 nm to 500 nm. In a further embodiment, the composition has a hydrodynamic diameter in a range of from 100 nm to 200 nm. In an even further embodiment, the composition has a hydrodynamic diameter of from 100 nm to 150 nm.

In an embodiment, the composition comprising a plant-derived nucleic acid and a bioactive agent, wherein the plant-derived nucleic acid is crosslinked with a cross-linking agent and wherein the bioactive agent is hydrophobic.

In an embodiment, the bioactive agent is an anti-cancer drug, an anti-inflammatory drug, a small molecule compound drug, an anti-virus drug, a vaccine or a combination thereof.

In an embodiment, the bioactive agent is an anti-cancer drug. In another embodiment, the anti-cancer drug is a chemotherapy drug. In a further embodiment, the anti-cancer drug is doxorubicin, cisplatin, carboplatin, etoposide, vinorelbine, topotecan, irinotecan, gemcitabine, uracil-tegafur, vinorelbinen, docetaxel, paclitaxel, prednisone, pemetrexed, gefitinib, erlotinib, cetuximab, bevacizumab or a combination thereof.

In an embodiment, the bioactive agent is an anti-virus drug. In a further embodiment, the anti-virus drug is a nucleic analog.

In an embodiment, the bioactive agent is an anti-inflammatory drug selected from the group consisting of zinc oxide, aspirin, ibuprofen, naproxen, meloxicam, celecoxib and indomethacin. In another embodiment, the vaccine may be composed of any immunogen that is able to elicit an immune response in the subject administered therewith, such as the surface antigen of a bacteria or a virus. In a further embodiment, the vaccine may be extracellular secreted protein A (espA) of enterohemorrhagic *Escherichia coli*, or hemagglutinin and neuraminidase of influenza virus.

In another aspect, the present disclosure provides a method of manufacturing a composition comprising crosslinked nucleic acids for delivery of the bioactive agent to a subject in need thereof. In an embodiment, the method comprises preparing an aqueous phase portion containing the plant-derived nucleic acid and the bioactive agent; preparing an oil phase portion containing a surfactant; mixing the aqueous phase portion and the oil phase portion to obtain an emulsified solution; sonicating the emulsified solution; and removing the oil phase portion to obtain the composition from the aqueous phase portion.

In still another aspect, the present disclosure provides a method of delivering the bioactive agent to a subject in need thereof. The method comprises orally administering the composition described above to a subject in need thereof, wherein the plant-derived nucleic acid crossed-linked to each other serves as a carrier of the bioactive agent in the composition.

BRIEF DESCRIPTION OF THE DRAWINGS

The present disclosure will become more readily appreciated by reference to the following descriptions in conjunction with accompanying drawings.

FIGS. 1A and 1C show the TEM images of DNA NGs; FIGS. 1B and 1D show the TEM images of DNA-DOX NGs; and FIG. 1E shows the TEM image of anthocyanin-loaded DNA NGs.

FIG. 4A shows the hydrodynamic diameter of DNA NGs and DNA-DOX NGs. FIG. 4B shows the zeta potential of DNA NGs and DNA-DOX NGs cross-linked by 3,3'-dithiobis(sulfosuccinimidyl propionate) (DTSSP) under different pH values in phosphate buffered saline (PBS, 0.01 N). FIG. 4C shows the cumulative DOX release of genipin-cross-linked DNA-DOX NGs under different pH values (pH 5.5 and 7.4). FIG. 4D shows the cumulative DOX release of DTSSP-cross-linked DNA-DOX NGs with or without GSH (0 and 10 mM) under different pH values (pH 5.5 and 7.4).

FIG. 7A shows the optical images of H1299 cells treated with various concentrations of free DOX, genipin-cross-linked DNA-DOX NGs and DTSSP-cross-linked DNA-DOX NGs for 20 h using light microscopy (original magnification×100, scale bar=50 µm).

FD: free DOX; DG: genipin-cross-linked DNA-DOX NGs; DD: DTSSP cross-linked DNA-DOX NGs.

Figure 9:
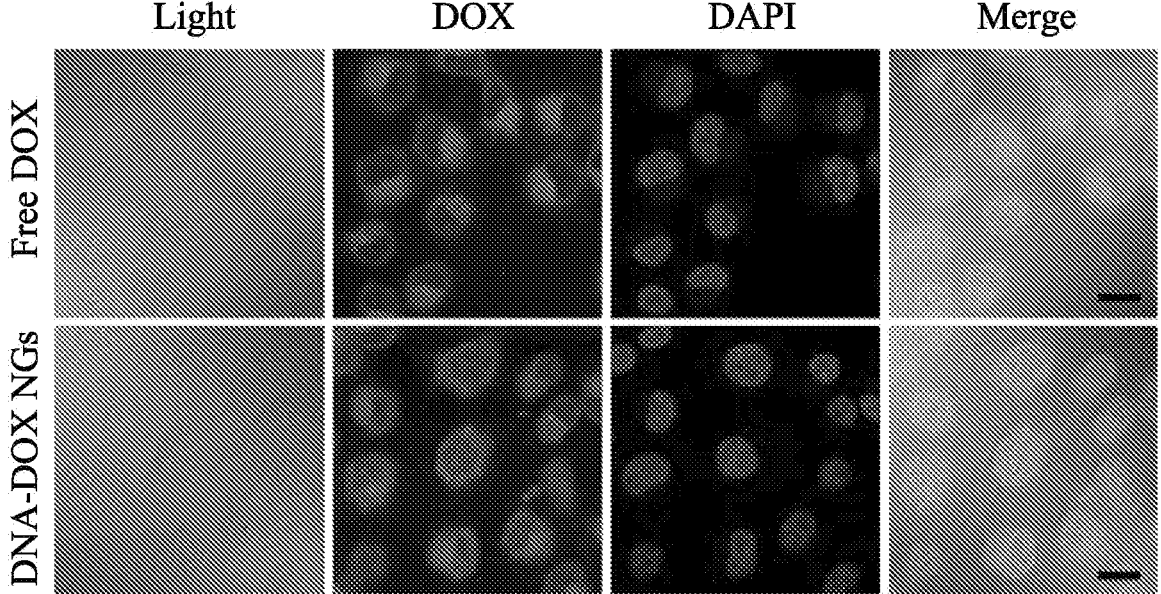

FIG. 9 shows fluorescent images of A549 cells after treatment of free DOX and DTSSP cross-linked DNA-DOX NGs of 5.0 µg/mL for 1 h, observed using confocal laser scanning microscope (scale bar=20 µm).

Figure 10A:
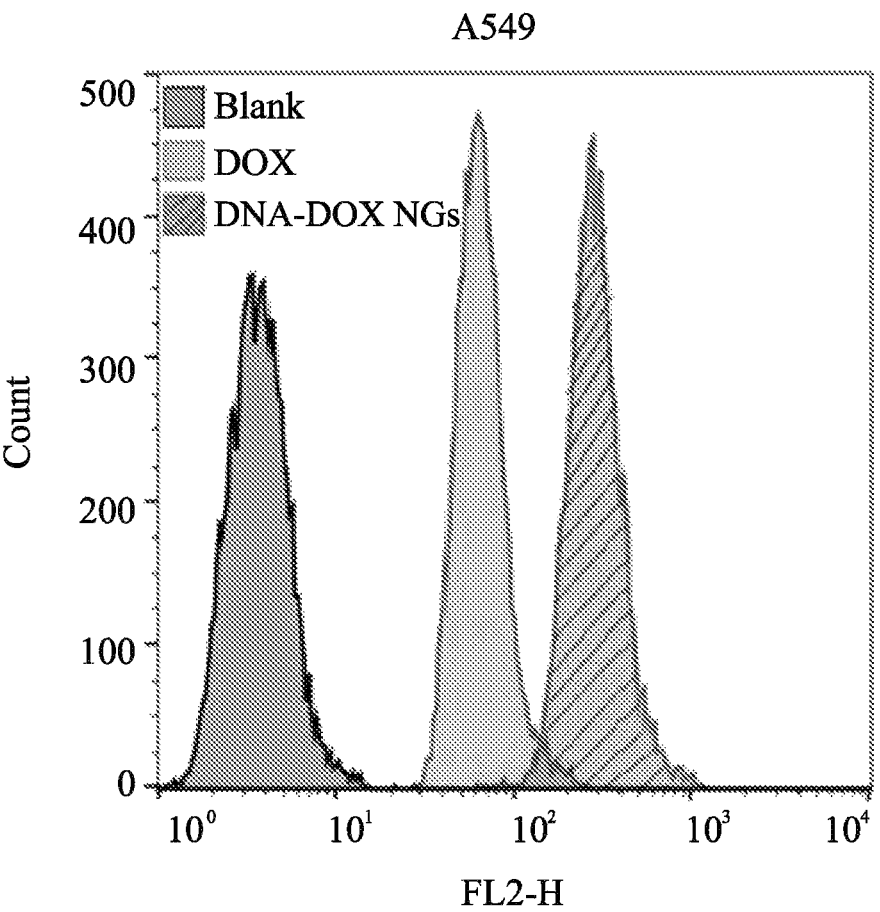
Figure 10B:
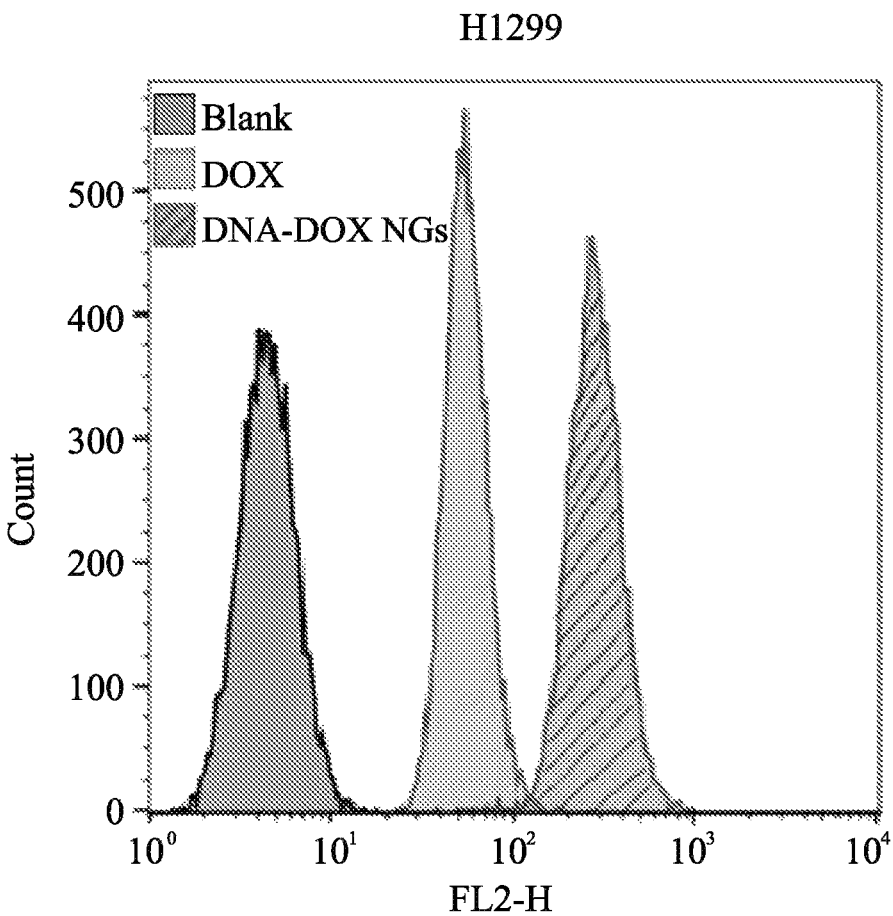
Figure 10C:
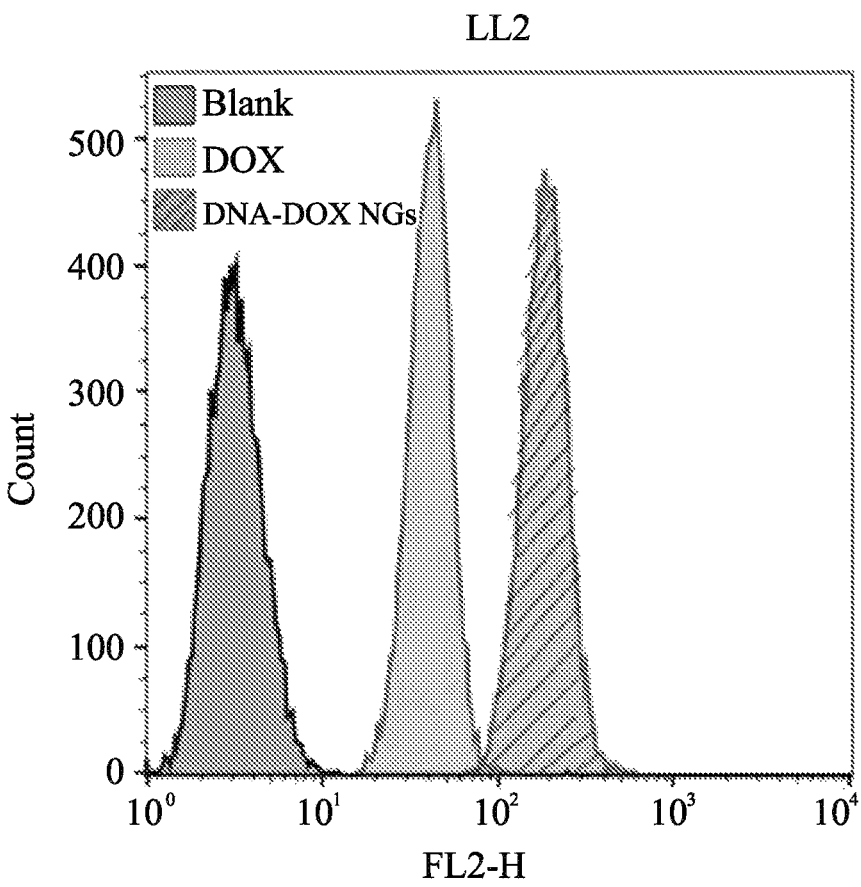
Figure 10D:
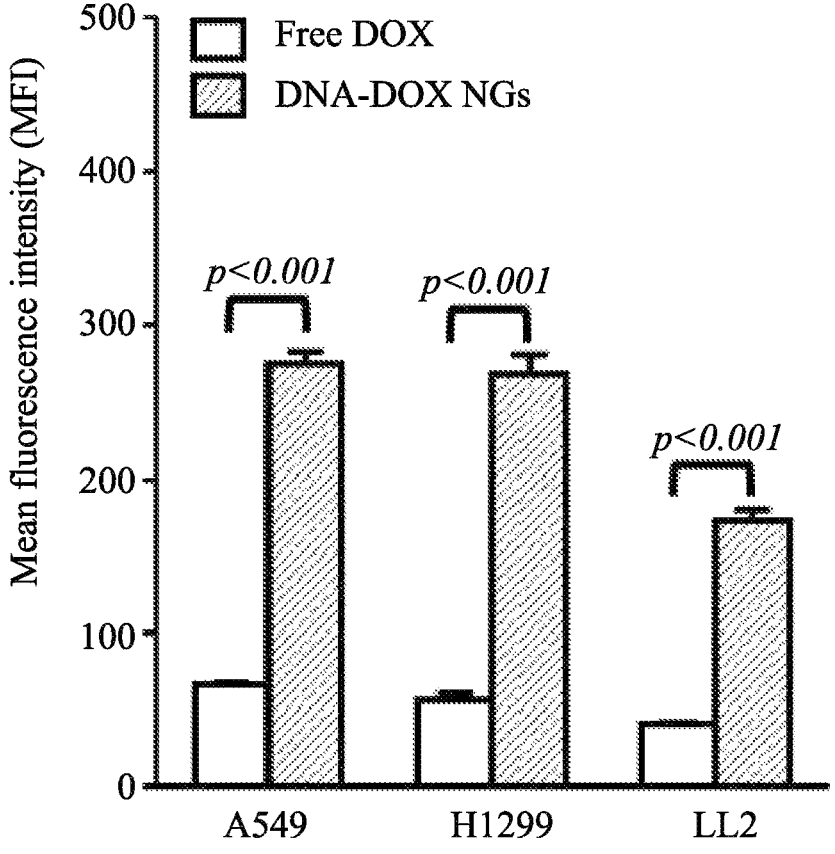

FIGS. 10A to 10D show the DOX fluorescence intensities of cancer cells after incubation with DOX and DTSSP-cross-linked DNA-DOX NGs having DOX concentration of 5.0 µg/mL for 1 h analyzed using flow cytometry. A549 cells in FIG. 10A, H1299 cells in FIG. 10B and LL2 cells in FIG. 10C. FIG. 10D shows the quantitative analysis of the mean fluorescence intensity of DOX in A549, H1299 and LL2 cells.

Figure 11A:
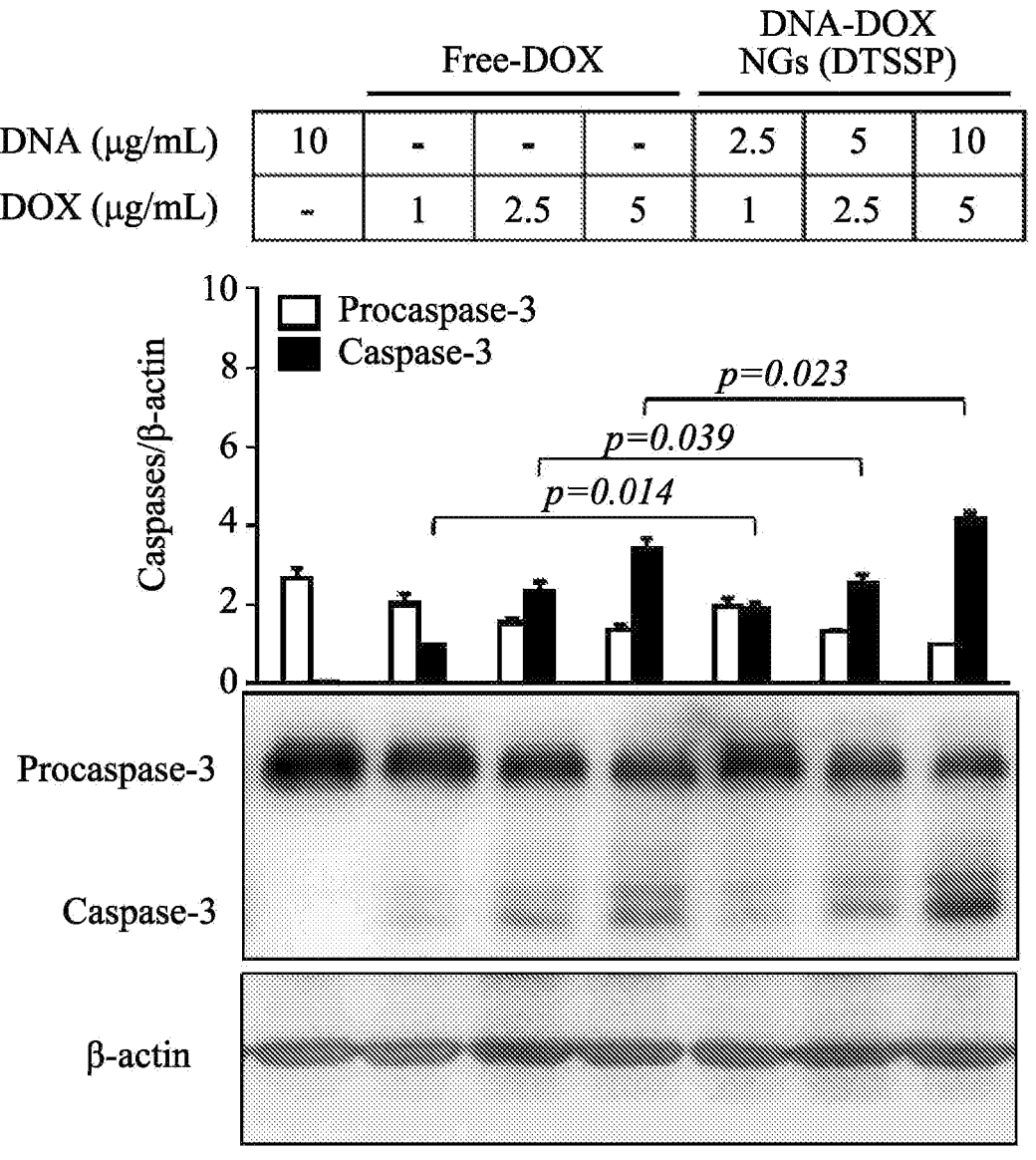
Figure 11B:
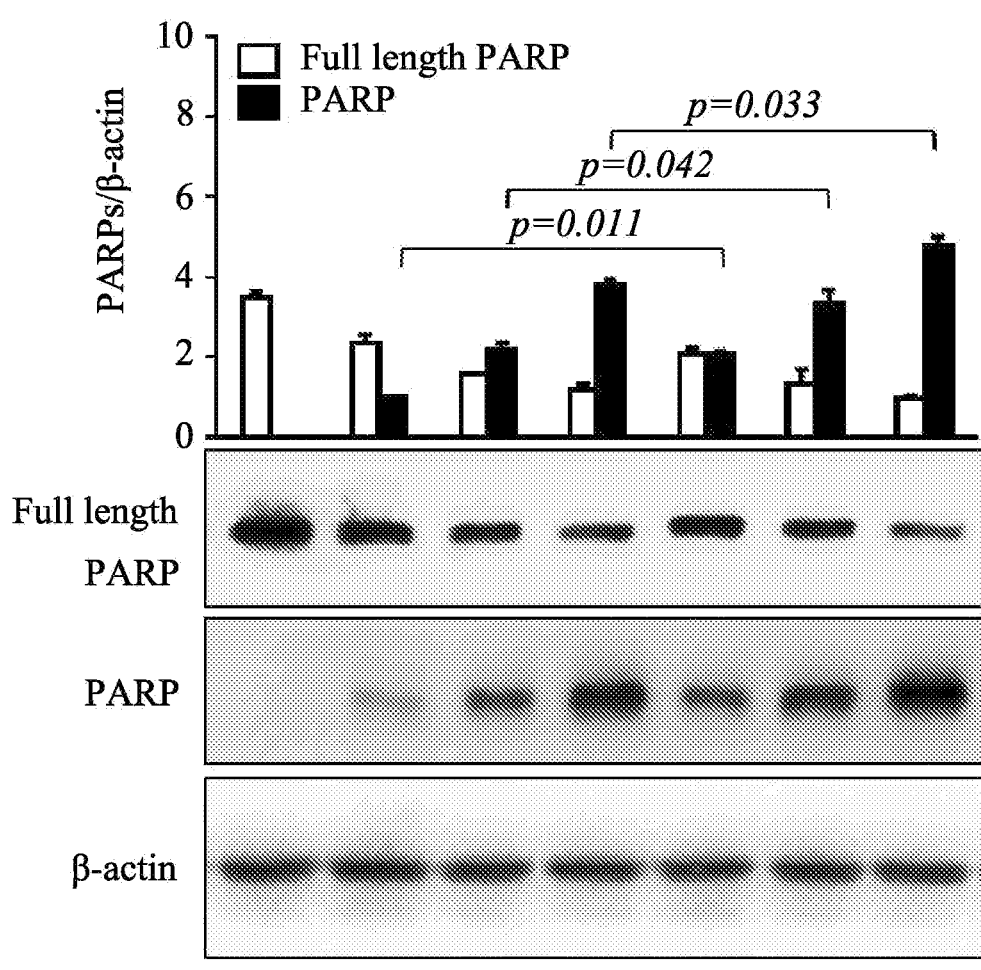

FIGS. 11A and 11B show histograms of the relative expression levels for the detection of procaspase-3, caspase-3, full length PARP and PARP. FIG. 11A shows histograms of the relative expression levels for the detection of procaspase-3, caspase-3 and cleaved caspase-3, and FIG. 11B shows histograms of the relative expression levels for the detection of full length PARP and PARP. H1299 cells were treated with or without various concentrations of DNA NGs, free DOX, and DTSSP cross-linked DNA-DOX NGs for 24 h. Expressions of procaspase-3, caspase-3, full length PARP and PARP were detected by western blot. Histograms represent the relative expression levels quantified by densitometric analysis using ImageJ software and normalized according to the β-actin reference bands. All data were statistically analyzed using an Unpaired Student's t test (n=3).

Figure 12:
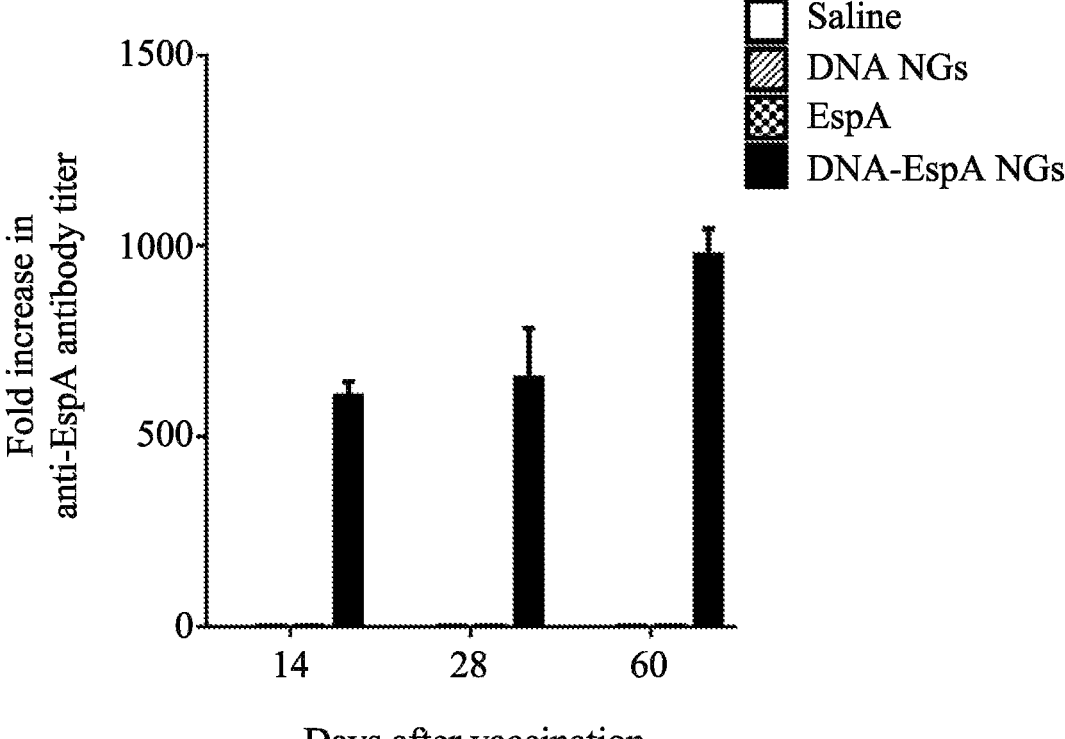

FIG. 12 shows histograms of anti-EspA antibody titers detected by ELISA after administration of saline, DNA NGs, EspA protein and DNA-EspA NGs in C57BL/6 mice (n=6 to 8). ELISA was carried out at 14, 28, and 60 days after vaccination.

DETAILED DESCRIPTION

The present disclosure provides a composition and a method of manufacture thereof to enhance the delivery of a bioactive agent to a subject in need thereof, e.g., the delivery of a bioactive agent to cancer cells. The composition of the present disclosure provides better target-specificity to deliver the bioactive agent and provides higher cytotoxicity to target cells, such as cancer cells.

In cancer cells, the pH value has been found to be more acidic than the extracellular matrix, while the content of intracellular glutathione (GSH) has also been found to be 1,000 times higher than the extracellular plasma. Accordingly, pH-responsive and/or reductive drug nanocarriers that can enable specific release of an encapsulated drug at a target site and thereby improve the anticancer activity are preferred in cancer drug delivery.

Use of non-toxic biomaterials as drug carriers is beneficial for the preparation of chemotherapeutic agents. Biomolecules isolated from nature such as saccharides, proteins, lipids and nucleic acids are suitable biomaterial candidates for the preparation of green biomedical reagents, because such naturally-derived materials have less biocompatibility and cytotoxicity issues in human bodies. Among these, deoxyribonucleic acid (DNA) is made up of nucleotides containing a nitrogen base, a phosphate group, and a sugar group. The types of nitrogen bases are adenine (A), thymine (T), cytosine (C) and guanine (G), and their specific sequences form the genetic code that determines amino acid sequences in proteins. A, C and G, in specific, have primary amines ($NH_2$) that can be reacted using cross-linking agents to form network structures suitable for drug encapsulation. Additionally, glutathione (GSH) in cancer cells effectively cleaves disulfide crosslinkers in these network structures, thereby releasing the encapsulated drugs in cancer cells.

Drug-loaded nanogels (NGs) can be prepared by mixing DNA strands, cisplatin and doxorubicin (DOX). DOX can intercalate between the GC bases of DNA. Thus, GC-rich sequences have been added into DNA segments to efficiently encapsulate DOX into DNA nanostructures. Distinct from the base pairing strategy, the present disclosure adopts a DNA crosslinking strategy that is less reliant on DNA sequences to build DNA nanocarriers. These as-prepared DNA NGs are expected not only to exhibit high biocompatibility to normal cells but to be also capable of efficiently releasing DOX within cancer cells and enhance apoptotic cell death.

In the present disclosure, the disulfide cross-linked DNA NGs exhibit pH- and reduction-sensitive properties useful for the delivery of anticancer drugs. The biocompatible and biodegradable DNAs that were selected as the main component of the NGs were extracted from fruits, e.g., kiwifruit. The cross-linking reaction not only enhanced the stability of the NGs but also rendered the NGs sensitive to reduction. Additionally, the nitrogen bases in the nucleotides facilitated the as-prepared NGs to present a hydrophobic nature, thereby enhancing hydrophobic interactions with the plasma membrane. On the other hand, the phosphate group present in the DNA backbone carries a negative charge that facilitates solubility in body fluid and is non-toxic to normal cells.

In the present disclosure, DNAs were used to prepare NGs by cross-linking of amino groups on nitrogen bases (A, C and G) using a cross-linking agent, such as genipin or 3,3'-dithiobis(sulfosuccinimidyl propionate) (DTSSP). The DNA NGs thus prepared is pH- and reduction-responsive, and act as efficient drug nanocarriers for intracellular drug delivery. The formation of disulfide cross-linking can afford the stabilization of NGs and the encapsulation of drugs. Moreover, the efficient DOX encapsulation is originated from the intercalation of DOX and the GC bases of DNAs as well as the electrostatic interactions. The dissociation of the NGs at the acidic and reductive environments triggered the release of drugs and consequently the inhibition of cancer cell growth.

As used herein, the terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list. As used herein, the term "or" is used interchangeably with the term "and/or" unless the context clearly indicates otherwise.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The terms "subject," "patient" and "individual" are used interchangeably herein and refer to a warm-blooded animal, such as a mammal that is afflicted with, or suspected of having, at risk for or being pre-disposed to, or being screened for cancer, e.g., actual or suspected cancer. These terms include, but are not limited to, domestic animals, sports animals, primates and humans. For example, the terms refer to a human.

It is further noted that, as used in this disclosure, the singular forms "a," "an," and "the" include plural referents unless expressly and unequivocally limited to one referent.

The term "nucleic acid" as used herein is meant any homopolymer or heteropolymer of deoxyribonucleosides, ribonucleosides, or nucleoside analogs. The nucleoside analogs can be any compound known in the art to be or subsequently discovered to be useful as a structural analog of a ribonucleoside or a deoxyribonucleoside. Nucleoside analogs include nucleotides comprising bases other than the five biologically occurring bases (adenine, guanine, thymine, cytosine and uracil). The monomers of the nucleic acid can be connected by phosphodiester linkages or modified linkages such as phosphotriester, phosphoramidate, siloxane, carbonate, carboxymethyl ester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A material is "biocompatible" with respect to an animal if the presence of the material in the animal is not injurious to the animal. By way of example, a biocompatible material does not induce an immune response to the animal when the material is administered to the body of an animal.

A material is "biodegradable" if the material undergoes decomposition when being in contact with a biological system upon administration to an animal. The decomposition can be evidenced, for example, by dissolution, depolymerization, disintegration, or by another chemical or physical change whereby the bulk of the material in the biological system is reduced over time. Such decomposition can be, but is not necessarily, catalyzed by a component of the biological system (e.g., an enzyme).

The "hydrodynamic diameter" of an object such as a molecule or a particle refers to the diameter of an imaginary sphere which is traced by rotating the object in all directions around its center of mass. The hydrodynamic diameter can be thought of roughly as the "effective size" of an object rotating rapidly in space or in a solution. By way of example, the hydrodynamic diameter of a sphere is the actual diameter of the sphere, and the hydrodynamic diameter of a rigid rod-shaped object is the length of the object along its longest axis (i.e., the length of the rod).

The "bioactive agent" refers to an agent to be delivered in a subject to treat a disease, such as cancer. The bioactive agent can be a drug or any substance that could deliver a therapeutical, immunological, nutritional or hygienical effect to the subject when being delivered into the subject and in contact with the cells of the subject.

The term "vaccine" as used herein is meant any material that induces immune response, immunological or immunogenic response to the subject being administered with the vaccine. The term "immune response," "immunological response" or "immunogenic response" means, but is not limited to, the development of a cellular and/or antibody-mediated immune response in the subject. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the DNA NGs as described herein. The host will display either a therapeutic or a protective immunological (memory) response such that resistance to new infection will be enhanced and/or the clinical severity of the disease will be reduced. Such protection will be demonstrated by either a reduction in number of symptoms, severity of symptoms, or the lack of one or more of the symptoms associated with the infection.

As used herein, the term "surfactant" may be cationic, anionic or non-ionic. Examples of surfactants include Span20, Span40, Tween80, Tween100, Triton100, Tergitol.

EXAMPLE

Exemplary embodiments of the present disclosure are further described in the following examples, which do not limit the scope of the present disclosure.

The following examples describe the compositions comprising plant-derived nucleic acids and bioactive agents and the methods of manufacture thereof.

The reagents, materials and procedures used in the following examples are as followed.

Reagents and Cells

Genipin and 3,3'-dithiobis(sulfosuccinimidyl propionate) (DTSSP) were obtained from Wako Chemicals and 4C Pharma Scientific Inc., respectively. Dulbecco's Modified Minimal Essential Medium (DMEM) and fetal bovine serum were from Hyclone Laboratories Inc. Span 80, Tween 80, 4',6-diamidino-2-phenylindole (DAPI), doxorubicin hydrochloride (DOX, 99.9%) and antibody against β-actin were obtained from Sigma-Aldrich. WST-8 reagent came from Dojindo Labs. Antibodies against caspase-3 and cleaved caspase-3 were obtained from Cell Signaling, and antibody against poly (ADP-ribose) polymerase (PARP) was obtained from Santa Cruz. The A549 lung adenocarcinoma cells, BEAS-2B bronchial epithelial cells, H1299 non-small cell lung carcinoma cells and Lewis lung carcinoma (LL2) cells were all obtained from the Bioresource Collection and Research Center (Hsinchu, Taiwan).

Genomic DNA Purification

Doubly distilled water (ddH$_2$O, 100 mL) was added to peeled kiwi fruit (New Zealand, 100 g) and homogenized into a homogeneous solution. Neutral detergent (Micro-Scientific, 2.5 mL) was mixed with the solution for 10 minutes, and upon the addition of 5.0 mL NaCl solution (5.0 M), the resulting mixture was incubated for an extra 10 min. A final incubation period was done with addition of bromelain (Sigma-Aldrich, 20 mg) for 30 min. The mixture (15.0 mL) was filtered with 1.5 mm mesh and precipitated with 99% ethanol (Sigma-Aldrich, 30 mL) to obtain DNA extract. After freeze-drying, the DNA extract (100 mg) was mixed thoroughly with 500 μL CTAB buffer (10.0% cetyltrimethyl ammonium bromide (CTAB) in H$_2$O, 5.0 M NaCl, 0.5 M ethylenediaminetetraacetic acid (EDTA) (pH 8.0), 1 M Tris-Cl (pH 8.0), 3.0% polyvinylpyrrolidone (molecular weight: 40 kDa) and 0.2% 3-mercaptoethanol) in a 60° C. bath for 30 min. After centrifuging for 5 min at 14,000×g, the supernatant was transferred to a new tube, and 5.0 μL of RNase was added, allowing to incubate for 20 min at 32° C. A solution of chloroform/isoamyl alcohol (24:1) was added to the mixture in equal volume ratios and mixed thoroughly for 5 sec. Upon centrifugation, the supernatant was decanted into a new tube, and the extraction was repeated until the supernatant was clear. Cold isopropanol was added to precipitate the DNA at quantities equal to 70% the volume of the mixture and placed at −20° C. for 10 min. The sample was then centrifuged for 5 min at 14,000×g and washed with ice cold 70% ethanol solution. Finally, the pellet was allowed to dry to remove any remnants of alcohol, and then dissolved in ddH$_2$O for DNA nanogel (NG) preparation. The DNA's purity 1.71±0.043 was determined by its absorbance ratio (260/280) with a NanoDrop Spectrophotometer (ND-1000 UV/Vis-USA).

Instrumentation and Characterizations

The hydrodynamic diameter (size) and zeta potential measurements of NGs were conducted on an angle of 90 degrees using an ELSZ-1000 light scattering system (Otsukaelectronic, Japan). Transmission electron microscopy (TEM) and circular dichroism (CD) measurements were performed on a Hitachi H7500 microscope with a Tungsten lamp (excitation voltage: 120 kV) and a JASCO J-815 spectrometer over a wavelength range from 190 to 260 nm. Small-angle X-ray scattering (SAXS) measurements of NG solutions in quartz capillary tubes (diameter: 1 mm) were conducted at 25° C. on a Bruker NanoSTAR U diffractometer (Bruker AXS GmbH, Germany) calibrated with a standard sample of silver behenate. The background subtracted data was desmeared against the beam length profile of the source.

Evaluation of DOX Release In Vitro

A dialysis bag (molecular weight cut off (MWCO): 3.5 KDa) containing 3.0 mL DOX-loaded DNA NGs crosslinked by genipin or DTSSP were introduced into a glass beaker containing 30 mL phosphate buffered saline (PBS, 0.01 N, pH 5.5 or pH 7.4) with or without GSH (0 or 10 mM). The glass beaker was placed in a water bath and shaken at a speed of 100 rpm at 37±1° C. The dialysate was taken at the designated time and characterized by a UV-Vis S-3100 spectrophotometer (SCINCO) at a wavelength of 485 nm. The solution was then poured back to the vial and each experiment was performed triples.

Cell Culture and Cell Viability Assay

A549, BEAS-2B, H1299 and LL2 cells were cultured in 96-well plates at a density of 1×10$^4$ cells/well in DMEM supplemented with 2.0 mM L-glutamine, 50 μg/mL gentamicin, and 10% (v/v) fetal bovine serum at 37° C. in 5% CO$_2$. Cells were then treated with various concentrations of free DOX, DNA NGs, and DNA-DOX NGs. After 24 h incubation, cell proliferation was evaluated using a WST-8 reagent (Dojindo Molecular Laboratories, Japan). After transferring the supernatant to 96-well plates, the supernatant was measured on a VersaMax Microplate Reader (Molecular Devices, Sunnyvale, CA, USA) at the wavelength of 405 nm. Cell viability was determined using the following equation: cell viability (%)=[(Abs405 nm in the treated sample cells−Abs405 nm in blank)/(Abs405 nm in untreated control cells−Abs405 nm in blank)]×100, wherein Abs405 nm refers to absorbance at 405 nm.

Hemolysis Assay

Human red blood cells (hRBC) were centrifuged, washed three times with sterile saline (Jason, Taipei, Taiwan) and resuspended in saline. 100 μL of DNA NG solution was added to 100 μL of 10% (v/v) of RBC suspension solution in each well of sterile 96-well plates. After incubating for 1 h at 37° C., the mixtures were centrifuged at 1000×g for 5 min to give the supernatant. After transferring the supernatant to sterile 96-well plates, the hemoglobin release was determined by the absorbance at wavelength of 405 nm on a microplate reader. Zero and 100% hemolysis were determined in saline and 0.1% Triton X-100, respectively. The percentage of hemolysis was calculated using the following equation: percentage of hemolysis (%)=[(Abs405 nm in DNA NPs solution−Abs405 nm in saline)/(Abs405 nm in 0.1% Triton X-100−Abs405 nm in saline)]×100, wherein Abs405 nm refers to absorbance at 405 nm.

Cellular Uptake Assays

A549 cells were cultured at a density of $1.0×10^5$ cells/well in 12-well plates and incubated with free DOX or DNA-DOX NGs with 5.0 µg/mL of DOX for 1 h. Then, the cells were washed with PBS for 3 times and fixed with cold methanol for 10 min. Upon being counterstained with DAPI (0.1 µg/mL) for 10 min and washed with PBS for 3 times, an Olympus IX71 fluorescence microscope was used to observe the cellular localization and intracellular DOX. For flow cytometry analysis, upon being treated with trypsin and suspended in cold PBS, the mean fluorescence intensity of the treated cells ($1.0×10^4$ cells) was analyzed using a flow cytometry (FACS caliber, Becton Dickinson) based on the manufacturer's protocols.

Immunoblot Analysis

The cells were treated with various concentrations of DOX or DTSSP-cross-linked DNA NGs for 24 h, followed by washing with saline for 3 times and ending with homogenization using radioimmunoprecipitation assay (RIPA) lysis buffer (pH 8.0, 150 mM Tris-HCl, 50 mM NaCl, 50 mM NaF, 1.0 mM $Na_3VO_4$, 1.0 mM phenylmethylsulfonyl fluoride (PMSF), 2.0 mM EDTA, 20 µg/mL leupeptin, and 20 µg/mL aprotinin). The cell lysates were analyzed by immunoblotting with primary antibodies against caspase-3 (#9662, Cell Signaling), PARP (sc-53643, Santa Cruz) and β-actin (A3854, Sigma-Aldrich) followed by appropriate secondary antibodies. An enhanced chemiluminescence (ECL) kit (Pierce Biotechnology, Rockford, IL) was used to detect the immuno-reactive protein bands. Upon being normalized by the intensity of β-actin, the relative intensities of the protein bands were quantified by using Image J software.

Statistical Analysis

Results are presented as means±SEM (n=3). Statistical differences were analyzed using two-way ANOVA and unpaired Student's t test. P values of less than 0.05 were considered statistically significant.

Example 1: Synthesis of DNA Nanogels (NGs)

The DNA NGs were prepared by cross-linking of DNA using genipin or DTSSP in an emulsified solution. The preparation of DNA NGs was achieved by emulsifying water droplets containing genomic DNA in hexane using surfactants (Span 80 and Tween 80) as well as crosslinkers (genipin or DTSSP). Specifically, the aqueous phase was first prepared by dissolving DNA (5 mg) in de-ionized water (0.5 mL), which is then mixed immediately with an oil phase containing surfactants Tween 80 (50 mg) and Span 80 (100 mg) dissolved in 4.0 mL n-hexane. The emulsified solution was then stirred for 10 min followed by pulsing via a Sonics VCX 750 Vibra-Cell Ultra Sonics Processor (energy level: 700 kW) for 5 min in an ice bath with the sonication cycle set to pulses of 5 sec followed by a stop for 10 sec. The cross-linking agent containing genipin or DTSSP was added to the solutions and pulsed for additional 5 min. The molar ratio of the cross-linking agent to amino groups was set to be 0.5. After pulse sonication, the emulsified solution was stirred at 350 rpm for 24 h and then centrifuged at 7000 rpm (Hitachi, CT15E) for 1 min. The aqueous phase was obtained by removing the supernatant and further extracted by adding n-hexane. The complete removal of the surfactant was achieved by repeating the above process until the oil phase was colorless. The purified NGs were then dispersed in a saline solution followed by sonication.

Example 2: Preparation of Drug-Loaded DNA NGs

The procedures for preparing drug-loaded NGs were the same as above in preparing DNA NGs except the water phase further contains a drug. DOX- and anthocyanin-loaded NGs were prepared with the water phase containing 17.84 mg DOX and 5.0 mg anthocyanin in the water phase, in addition to 20 mg of genomic DNA, respectively. Drug-loading efficiency (mass of loaded drug/mass of added drug) for the DOX and anthocyanin loading was detected by absorbance at 485 nm and 500 nm, respectively.

Example 3: Characterization of DNA and DNA-DOX NGs

TEM analysis revealed that the DNA and drug-loaded DNA NGs exhibited spherical morphology, as shown in FIGS. 1A to 1E, and dynamic light scattering (DLS) analysis showed that their average sizes ranged between 100 and 150 nm (Table 1). It can be seen that the size of the DNA-DOX NGs was slightly larger than that of the DNA NGs alone. To observe the outer DNA shell of the DNA NGs, purple anthocyanin-loaded DNA NGs were prepared to better contrast with their contents. The results demonstrated that the sizes of anthocyanin-loaded DNA NGs were slightly larger than those of the DNA NGs (Table 1 and FIG. 1E). As shown in the TEM images, the sizes of the DNA NGs were smaller than those determined by DLS analysis possibly due to the shrinkage of the NGs upon drying (Table 1).

Figure 1A:
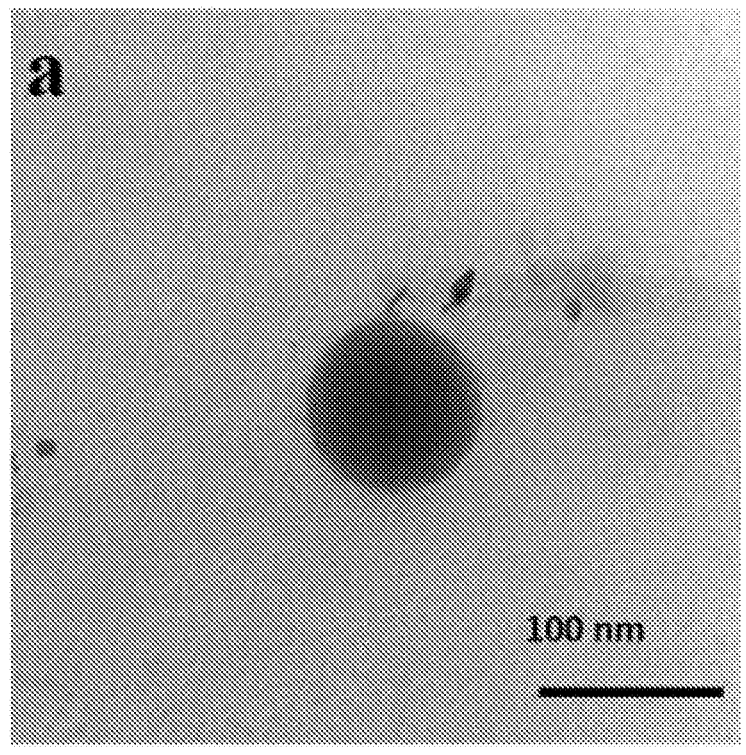
FIGS. 1A to 1E show the transmission electron microscopy (TEM) images of nanogels (NGs).
Figure 1B:
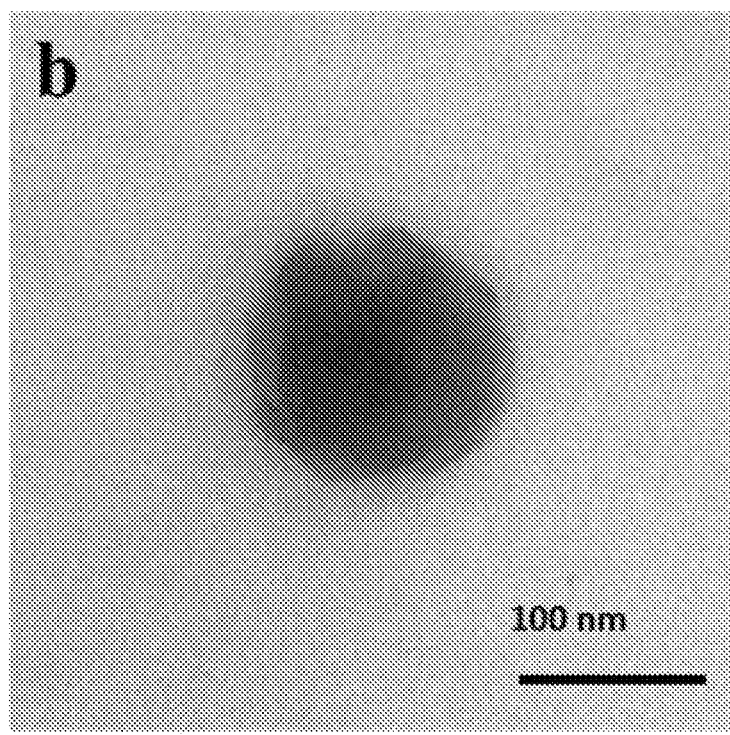
Figure 1C:
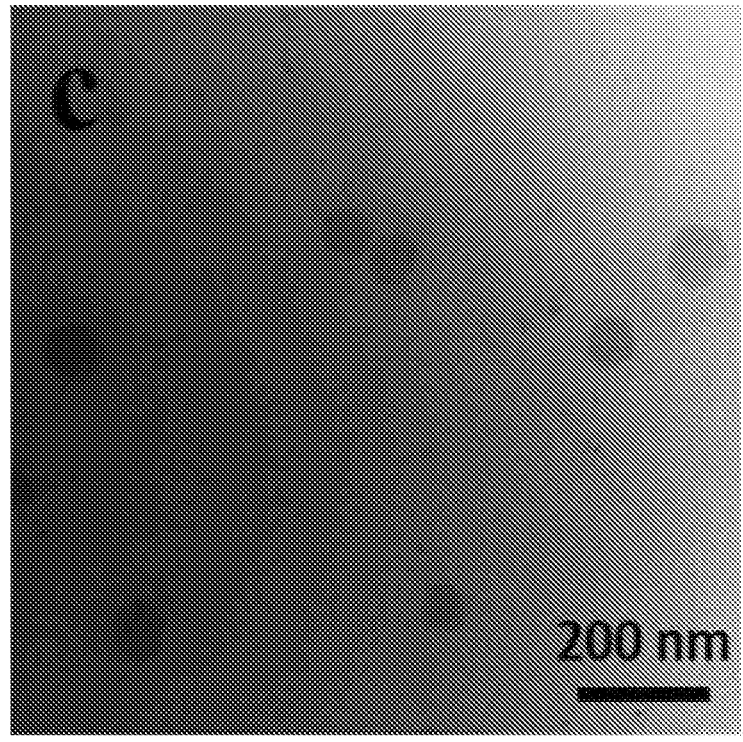
Figure 1D:
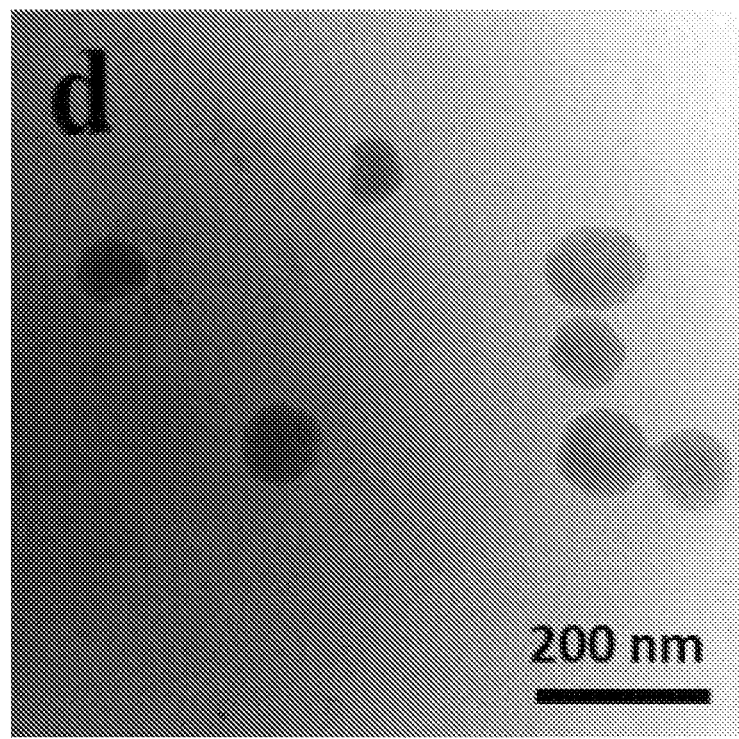
Figure 1E:
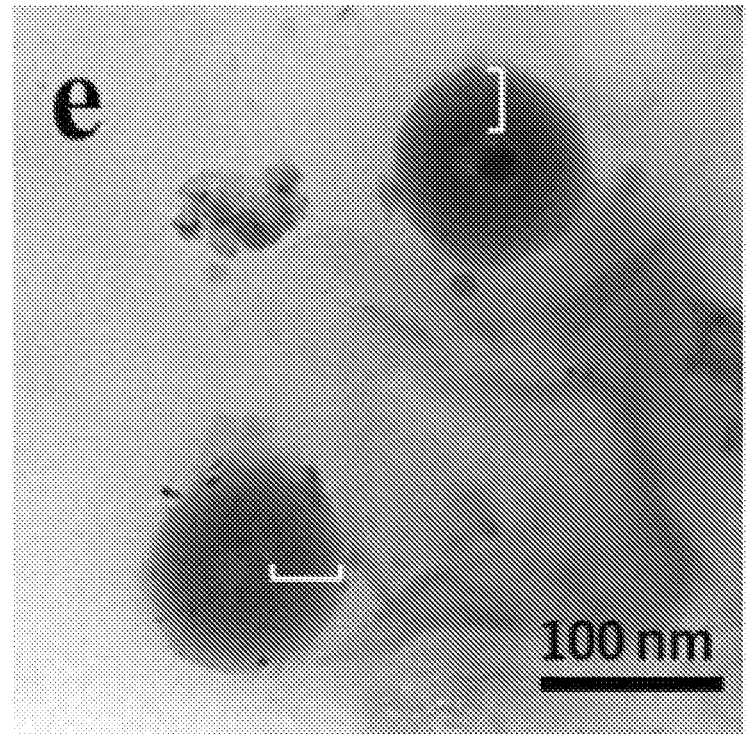
Figure 2:
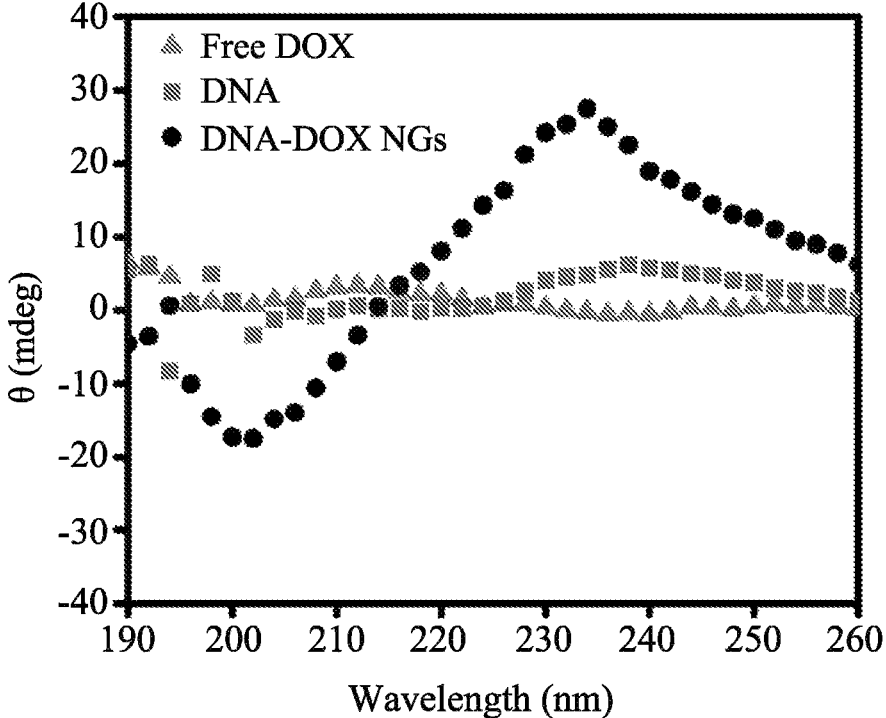
FIG. 2 shows the circular dichroism (CD) measurements of free DOX, genomic DNA, and DNA-DOX NGs.

CD analysis of the genomic DNA indicated the presence of a maximum at 238 nm. The CD spectrum of DNA-DOX NGs showed a maximum and minimum at 233 and 201 nm, respectively (FIG. 2). The shift of the maximum could be probably due to the presence of cross-linked genipin compounds. The DNA exhibited apparent conformational changes upon genipin cross-linking.

Figure 3:
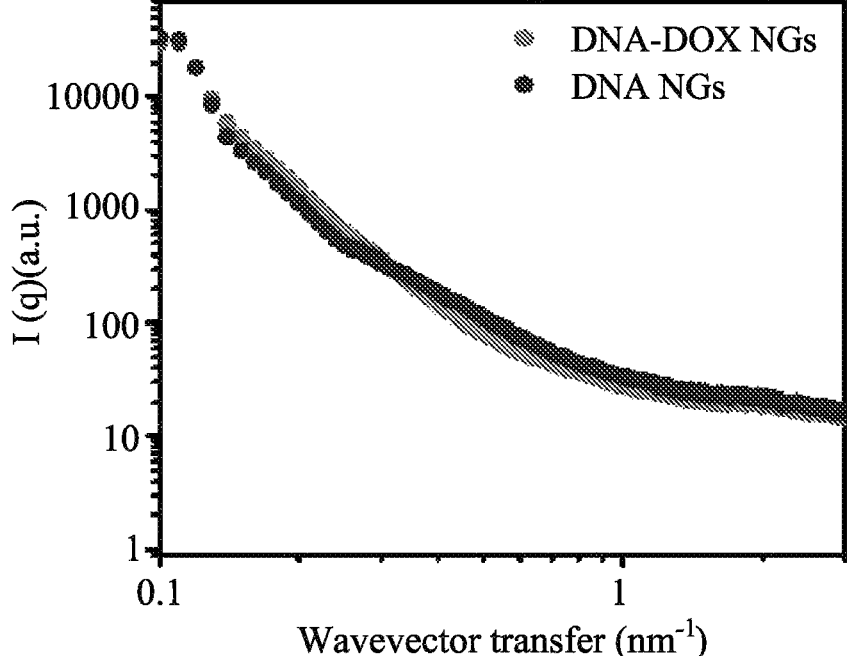
FIG. 3 shows the small-angle X-ray scattering (SAXS) measurements of DNA and DNA-DOX NGs.

The SAXS analysis of the DNA and DNA-DOX NGs indicated scattering intensities (I) with I (q) α $q^{-n}$ at low scattering vectors (q) of −4, indicating the formation of solid NGs (FIG. 3). Unlike the SAXS pattern of DNA-DOX NGs, the SAXS pattern of DNA NGs showed a broad hump at the scattering vector between 0.27 and 0.8 $nm^{-1}$, which could originate from the electron variations within the nanogel network.

Zeta potential measurements of these DNA NGs revealed that they carried negative charges with a high charge density, as can be seen by the negative zeta potential values, suggesting the presence of phosphate residues as responsible for such negative charge (Table 1).

TABLE 1

| Hydrodynamic diameter (size), polydispersity index (PDI), and zeta potential of DNA and drug-loaded NGs cross-linked by genipin or DTSSP in PBS (0.01N, pH 7.4) (n = 3) | | | | |
| --- | --- | --- | --- | --- |
| Sample | Cross-linker | Size (nm) | PDI | Zeta potential (mV) |
| DNA NGs | Genipin | 115.0 ± 2.98 | 0.269 ± 0.05 | −44.75 ± 2.24 |
| DNA-DOX NGs | | 139.3 ± 6.83 | 0.277 ± 0.06 | −43.26 ± 3.09 |
| anthocyanin-loaded DNA NGs | | 120.6 ± 4.19 | 0.212 ± 0.07 | −39.55 ± 2.17 |

TABLE 1-continued

Hydrodynamic diameter (size), polydispersity index (PDI),
and zeta potential of DNA and drug-loaded NGs cross-linked
by genipin or DTSSP in PBS (0.01N, pH 7.4) (n = 3)

| Sample | Cross-linker | Size (nm) | PDI | Zeta potential (mV) |
|--------|--------------|-----------|-----|---------------------|
| DNA NGs | DTSSP | 121 ± 3.76 | 0.234 ± 0.05 | −40.5 ± 2.89 |
| DNA-DOX NGs | | 142.6 ± 5.81 | 0.286 ± 0.07 | −42.7 ± 3.37 |

Example 4: Characterization of DNA NGs as Drug Nanocarriers

The use of DNA NGs as drug nanocarriers was evaluated upon loading DOX, an anticancer drug, into the NGs. The drug-loading efficiency of DOX was calculated to be 92.5±1.23% and 91.7±2.04% for genipin- and DTSSP-cross-linked NGs, respectively.

Figure 4A:
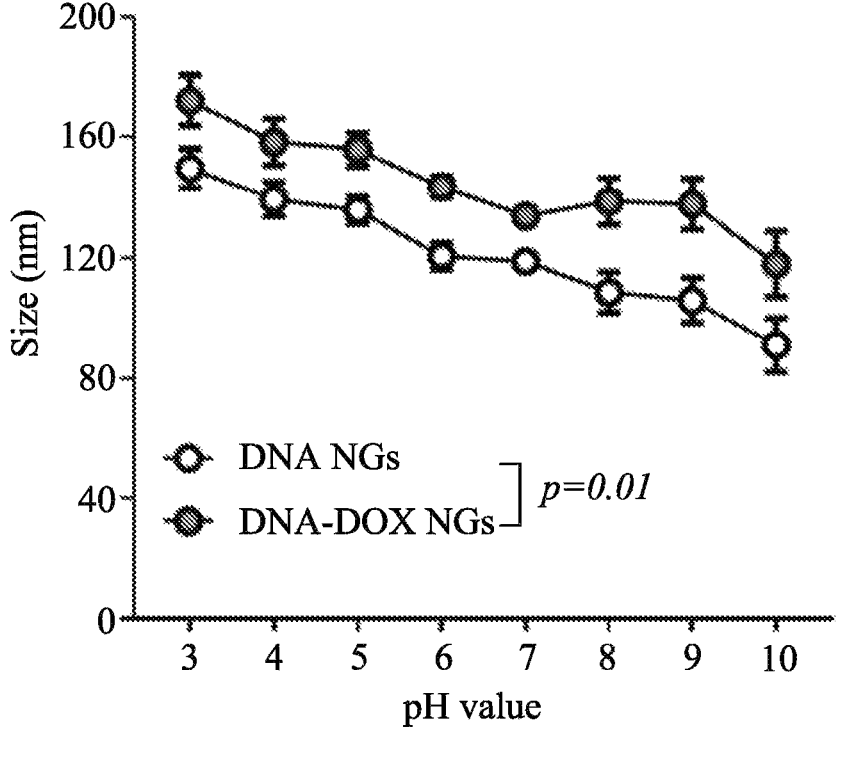
FIGS. 4A to 4D show the characterization of DNA NGs as drug nanocarriers.
Figure 4B:
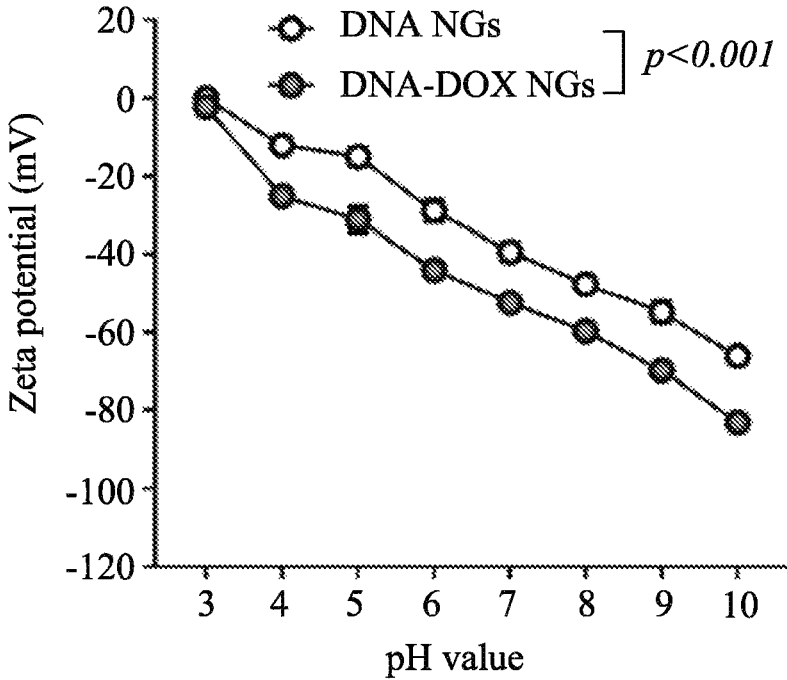

In order to evaluate the properties of DNA NGs and whether the DOX could be released from the DNA-DOX NGs in acidic cancerous environments, the effects of pH values on the size and zeta potential of DNA and DNA-DOX NGs were analyzed. As shown in FIG. 4A, the hydrodynamic diameters (sizes) of the NGs slightly decreased upon the increase of the solution pH. As shown in FIG. 4B, zeta potential measurements showed that all the NGs were negatively charged at the solution pH higher than 3.0, possibly due to the presence of phosphate groups. An apparent increase in overall negative charge was seen upon increasing the solution pH, which can mainly be attributed to the deprotonation of the phosphate groups ($H_2PO_4^-$ and $HPO_4^{2-}$). In addition, the size of DNA-DOX NGs appeared larger than that of DNA NGs, due to the incorporation of DOX. Zeta potential analysis showed that the DNA-DOX NGs exhibited more negatively charges than their parent counterparts, suggesting that the encapsulated DNA affected the surface properties of the as-prepared NGs.

Figure 4C:
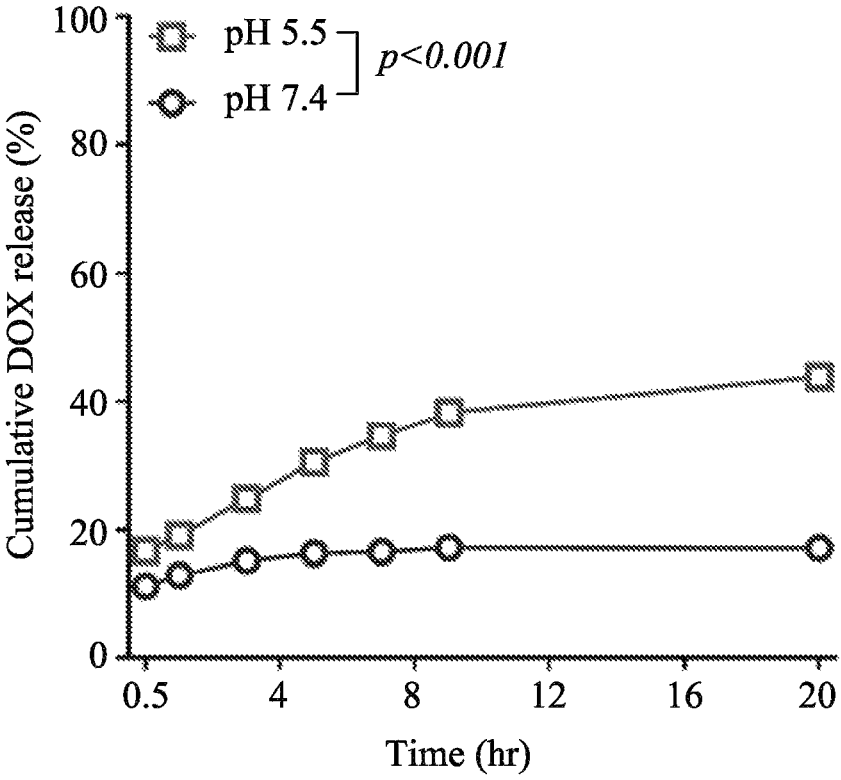
Figure 4D:
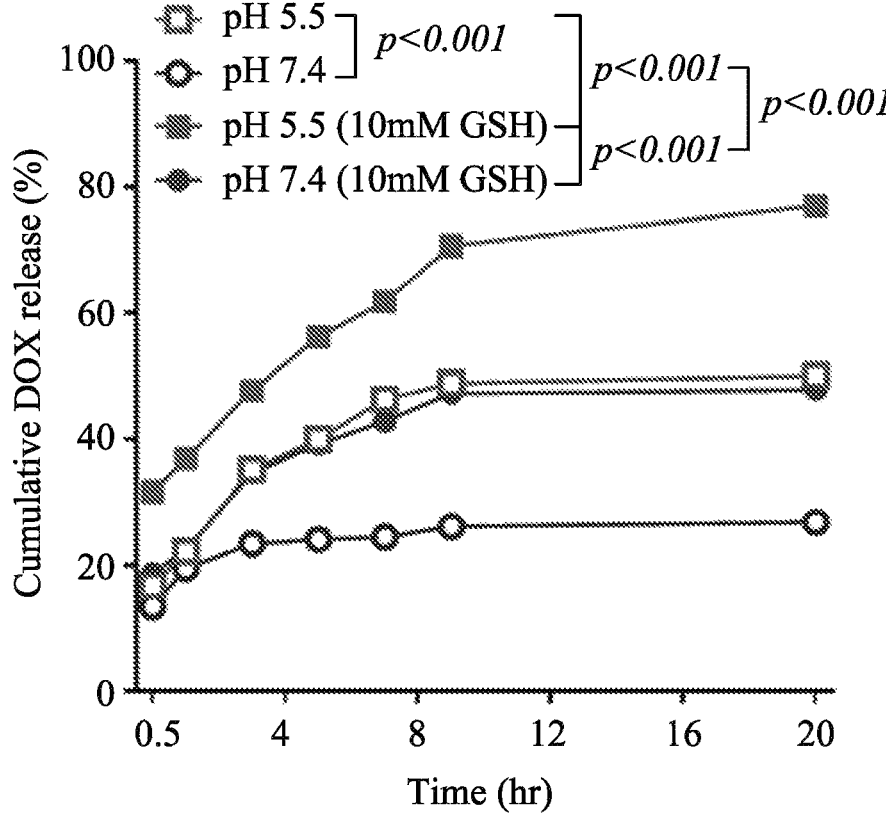

Moreover, the DOX releasing experiments for DNA-DOX NGs cross-linked by genipin or DTSSP at different solution conditions were conducted by measuring the absorbance at 485 nm at different time courses upon dialysis. As shown in FIGS. 4C and 4D, both the genipin- and DTSSP-cross-linked DNA-DOX NGs exhibited significantly greater DOX-releasing activity at pH 5.5 than at pH 7.4 (p<0.001). Furthermore, the DNA-DOX NGs at pH 7.4 exhibited no apparent burst release.

The reduction responsive DOX release from the DTSSP-cross-linked DNA-DOX NGs was then investigated at pH 5.5 and 7.4 in the presence of 10 mM GSH. As shown in FIG. 4D, the cumulative DOX release from the DNA-DOX NGs increased with time before the 12-hour time mark and was enhanced in the presence of 10 mM GSH (p<0.001). These results revealed that acidic environments facilitated the release of DOX probably due to the protonation of the phosphate groups ($HPO_4^{2-}$ and $PO_4^{3-}$), leading to the disruption of the DOX/DNA complexes formed via electrostatic interactions. The presence of GSH led to the de-cross-linking of the NGs and subsequently the enhanced release of the drugs.

Example 5: Cytotoxicity of DNA NGs as Drug Nanocarriers

Figure 5:
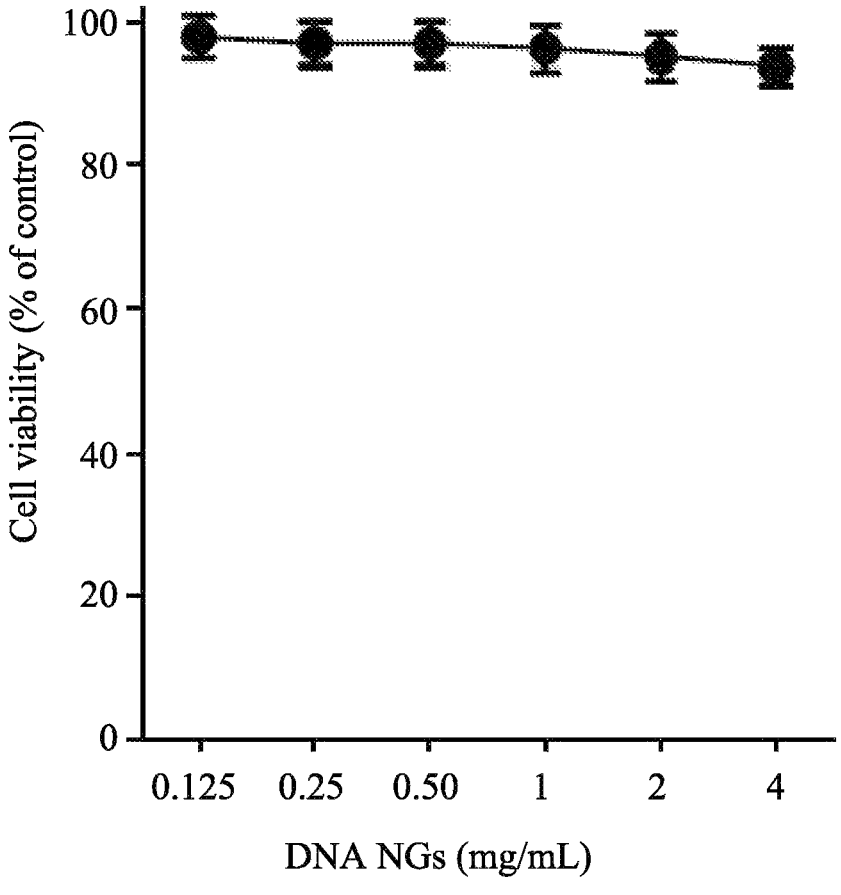
FIG. 5 shows the cell viability treated with DNA NGs.

The cytotoxic effects of free DOX, genipin-cross-linked DNA-DOX NGs, and DTSSP-cross-linked DNA-DOX NGs against BEAS-2B, A549, H1299, and LL2 cells were analyzed. As can be seen in FIG. 5, cell viabilities were calculated to be higher than 90% at DNA NGs concentration less than 4.0 mg/mL, revealing that the DNA NGs were barely cytotoxic toward those cells.

Figure 6:
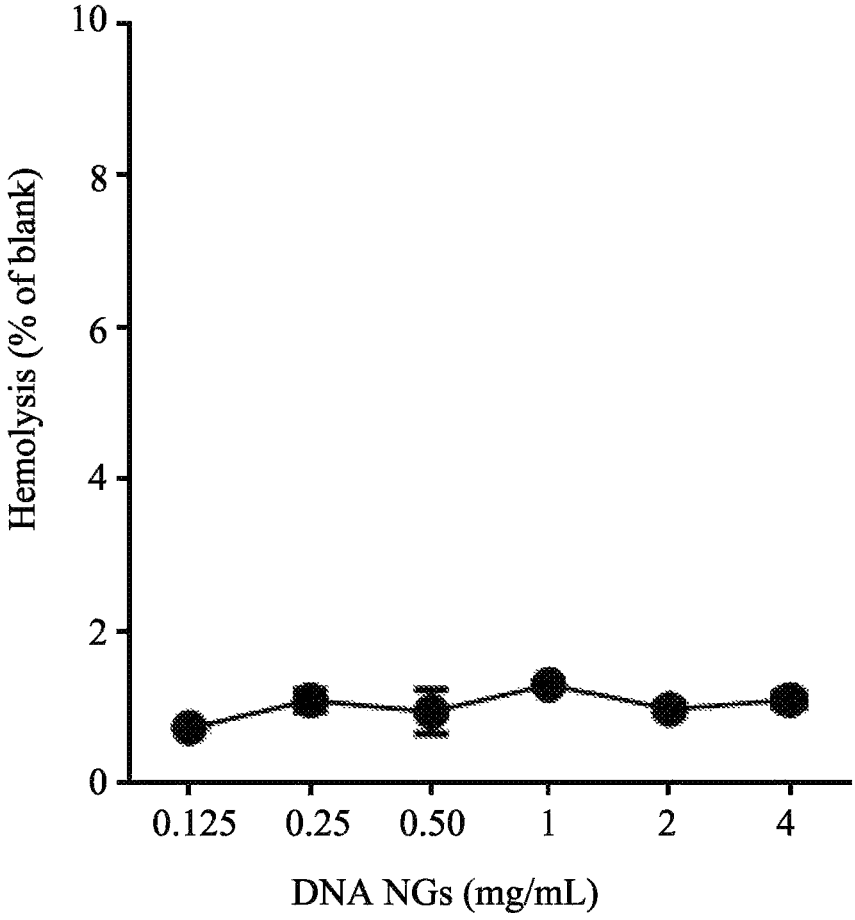
FIG. 6 shows the hemolysis percentage of human red blood cells (RBCs) treated with DNA NGs.

Further, as shown in FIG. 6, hemolytic activities of the DNA NGs exhibited low hemolytic activities against human RBCs.

Figure 7A:
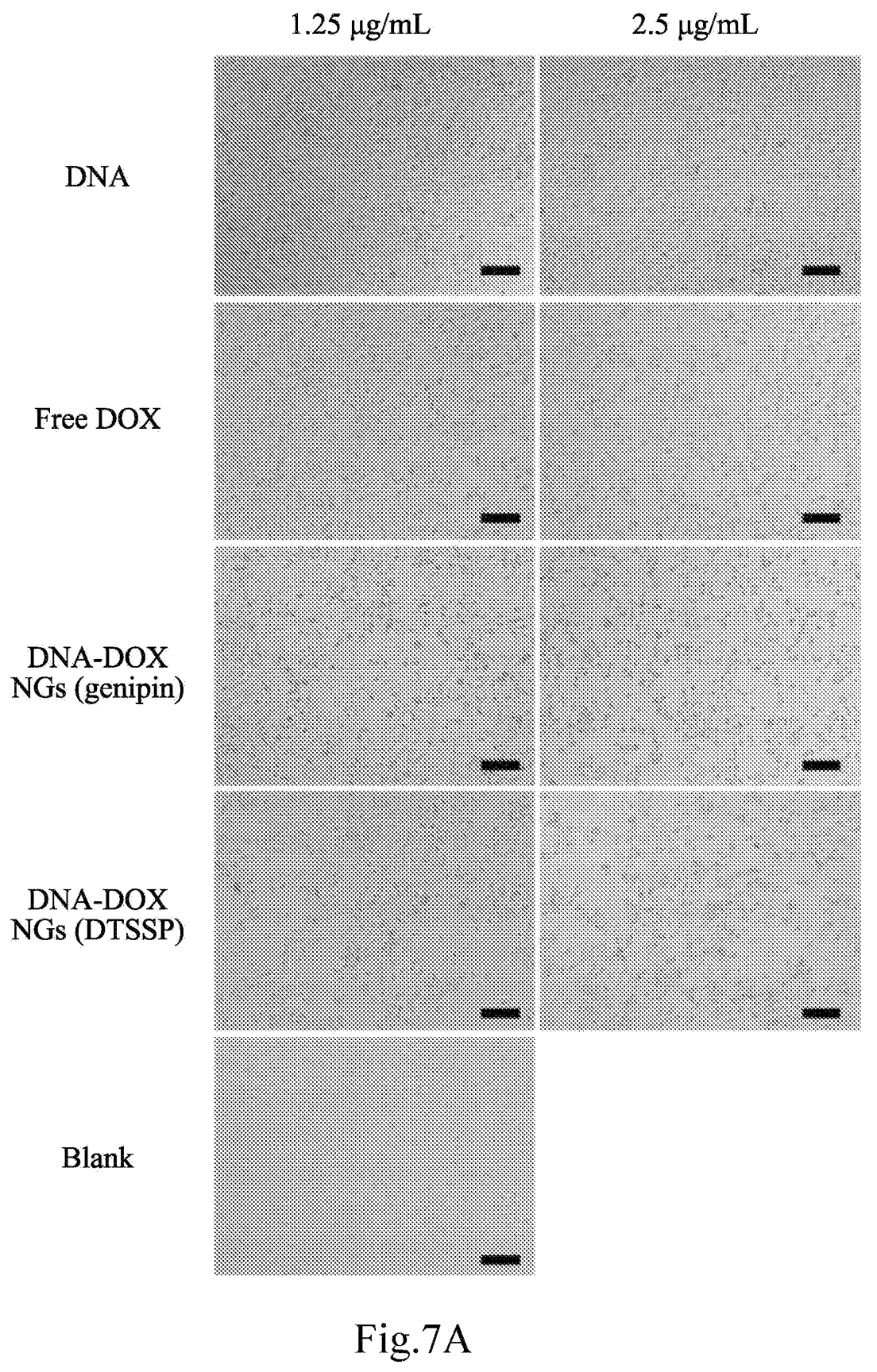
Figure 7B:
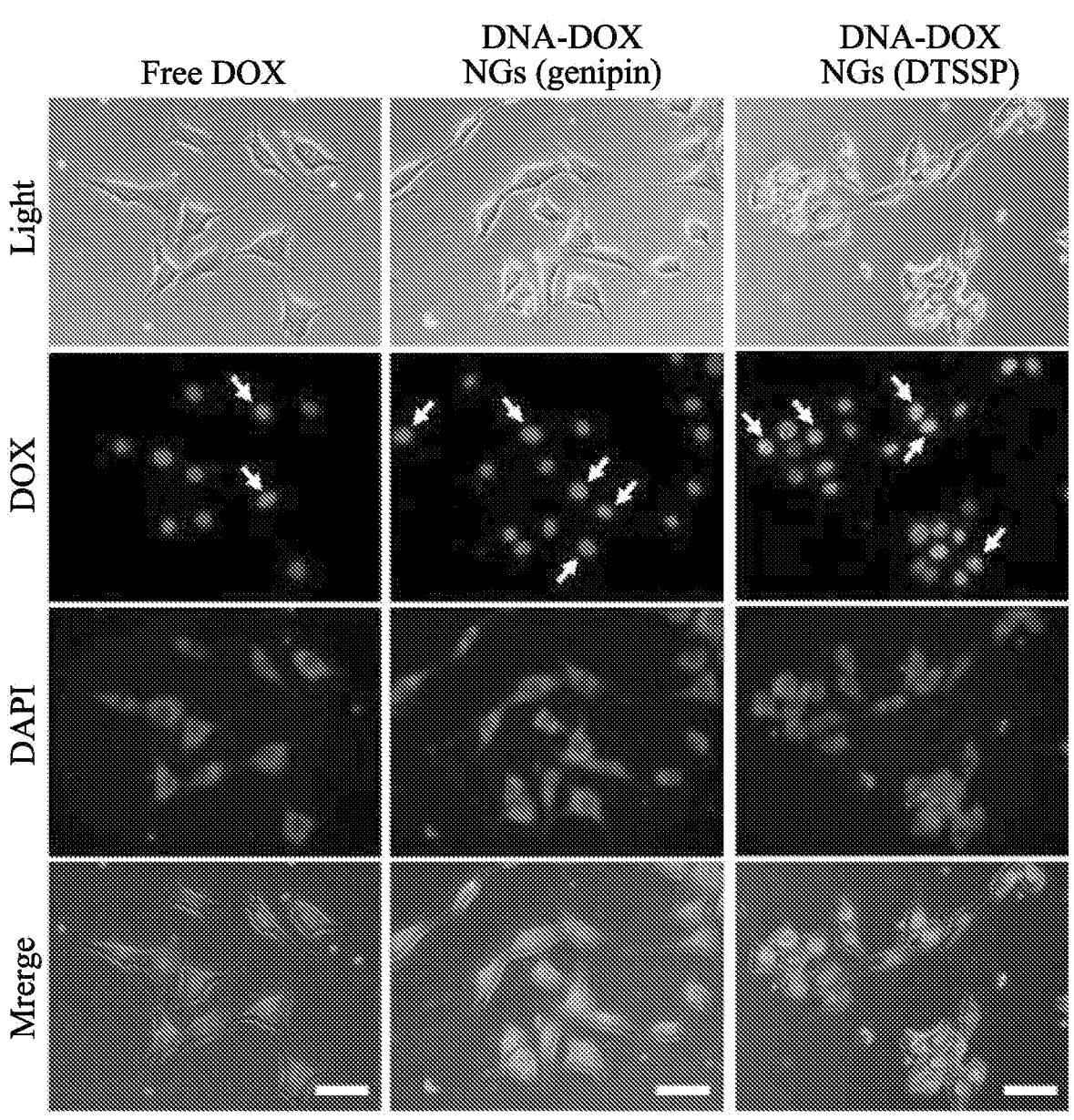
FIG. 7B shows the fluorescent images of A549 cells after treatment with DOX and DNA-DOX NGs of the same DOX concentration (1.25 µg/mL) for 18 h observed using inverted fluorescence microscopy (original magnification×400, scale bar=20 µm). The white arrows indicate the apoptotic chromatin condensation of the nuclei.
Figure 8A:
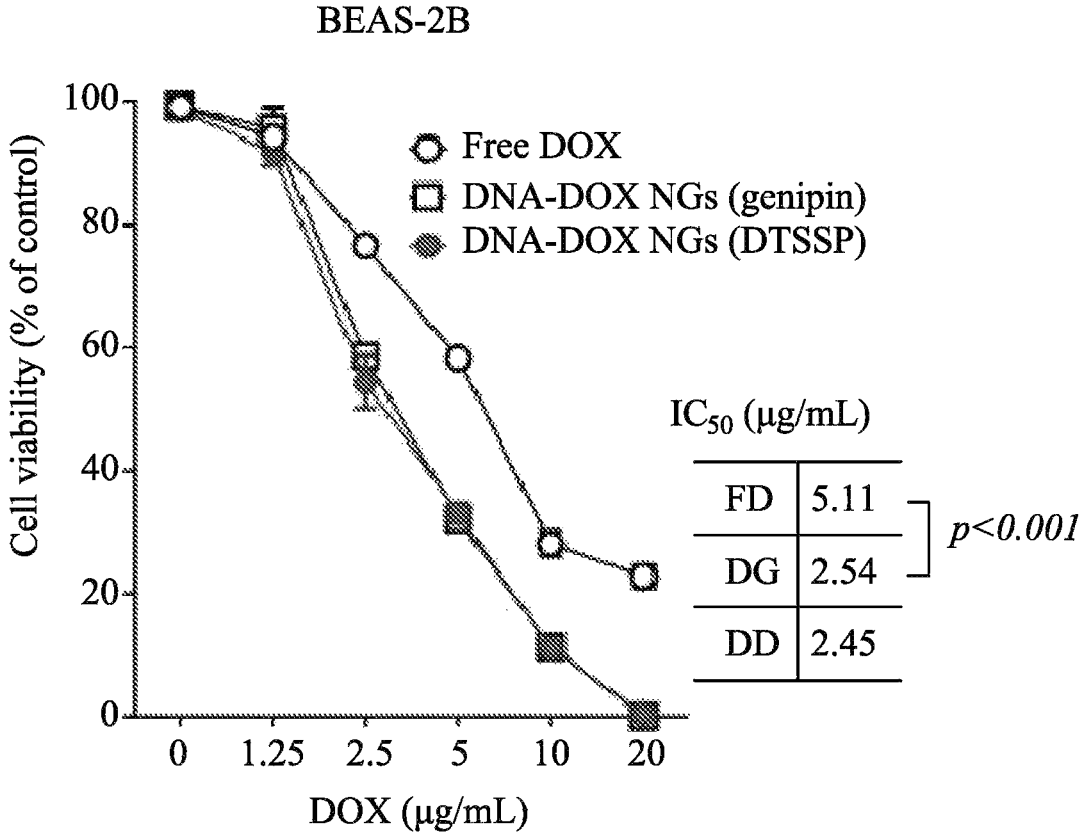
FIGS. 8A to 8D show the cell viability of non-cancer cells (BEAS-2B bronchial epithelial cells in FIG. 8A) and cancer cells (A549 lung adenocarcinoma cells in FIG. 8B, H1299 non-small cell lung carcinoma cells in FIG. 8C, and LL2 Lewis lung carcinoma cells in FIG. 8D) in the presence of free DOX and DNA-DOX NGs. Cells were treated with various concentrations of free DOX and DNA-DOX NGs for 24 h. Cell proliferation was measured by WST-8 assay, and $IC_{50}$ values are shown in the right panel. All data were statistically analyzed using two-way ANOVA tests (n=3).
Figure 8B:
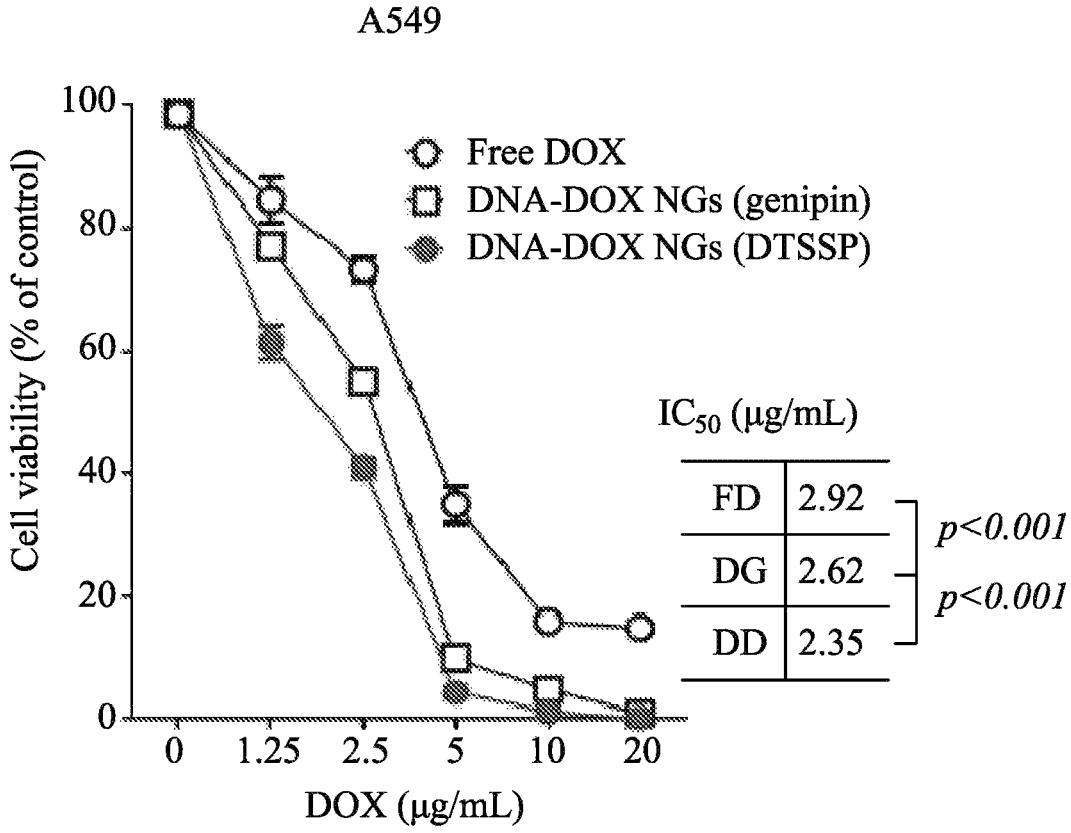
Figure 8C:
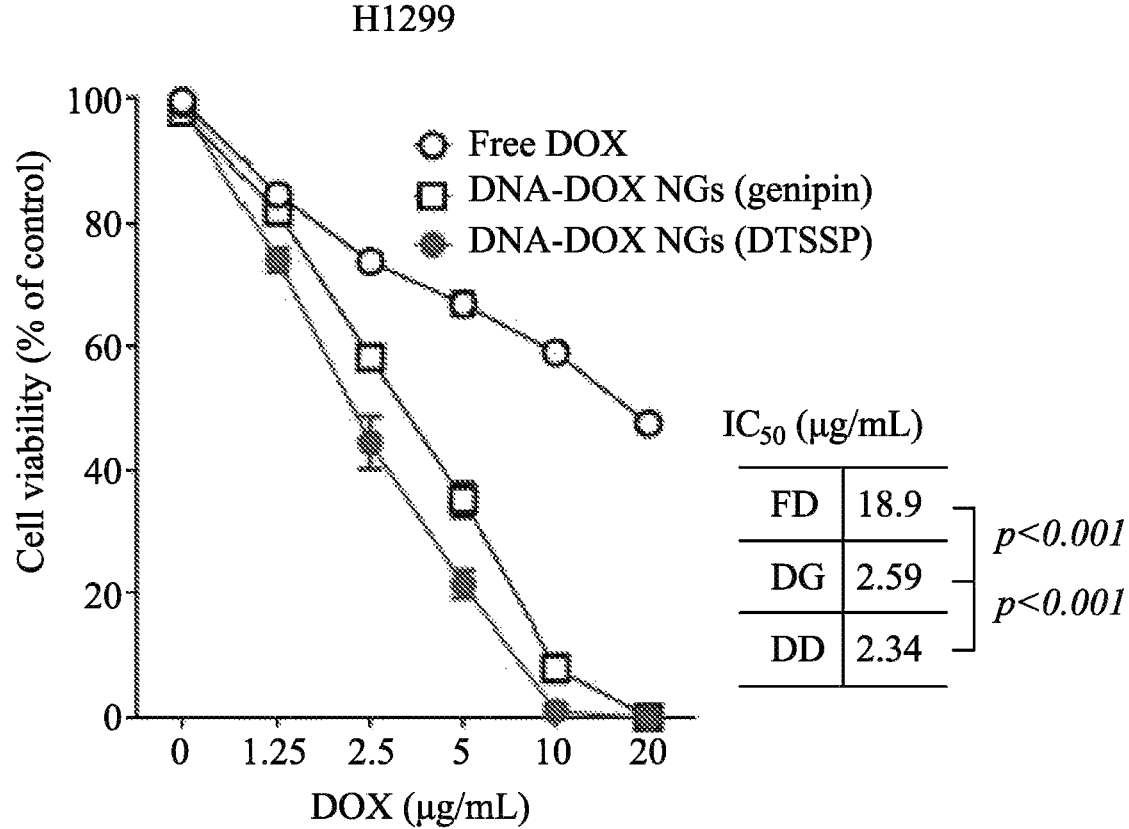
Figure 8D:
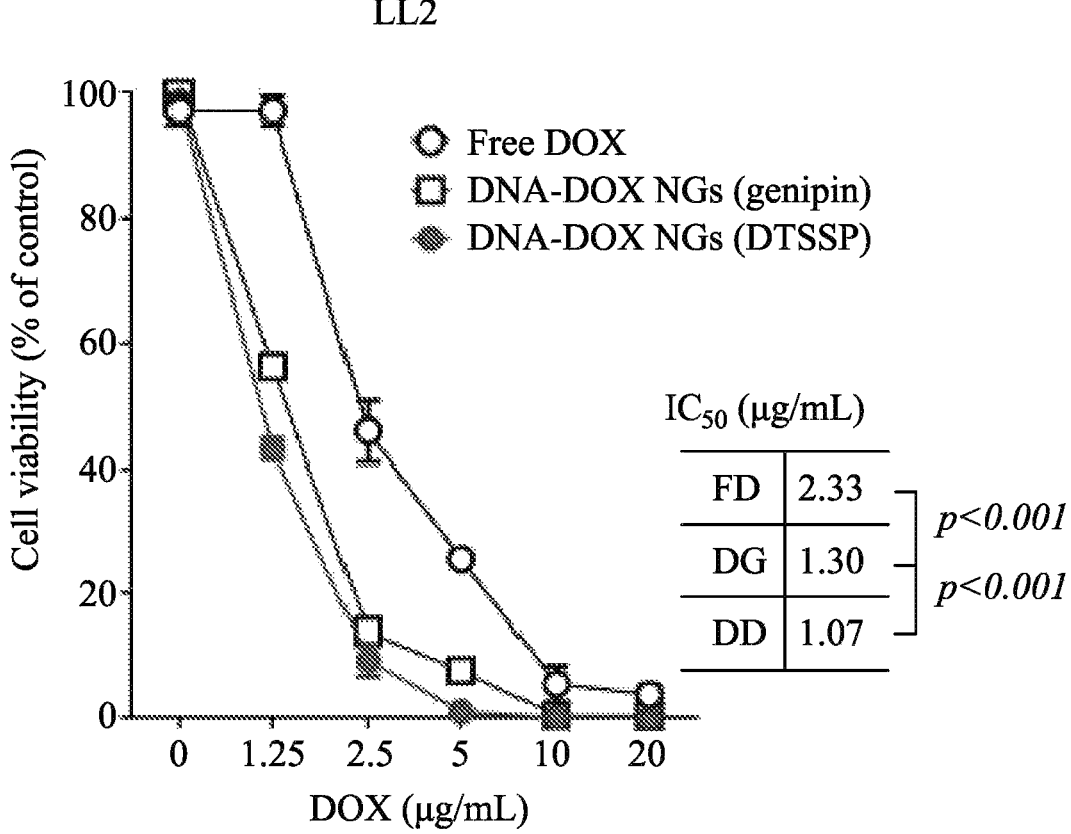

Next, the morphologies of H1299 cells after treatment with free DOX and DNA-DOX NGs cross-linked by genipin or DTSSP at two concentrations of DOX (1.25 or 2.5 μg/mL) were analyzed using light microscopy. As shown in FIG. 7A, cells treated with DNA NGs grew just as well as the control group. Compared to the DOX-treated groups, cells treated with DNA-DOX NGs exhibited relatively ill-defined morphologies than those treated with free DOX group. Moreover, cells treated with DTSSP-cross-linked DNA-DOX NGs were fewer in number than those treated with genipin-cross-linked counterparts. FIG. 7B showed apoptotic chromatin condensation of the nuclei in the cells treated with DNA-DOX NGs for 18 hours.

The cytotoxicity of free DOX and cross-linked DNA-DOX NGs against these cells was shown in FIGS. 8A to 8D, and the $IC_{50}$ values were listed in Table 2. These results demonstrate that the cytotoxicity of both free DOX and DNA-DOX NGs were dependent on concentrations. After treatment with various concentrations for 24 h, the DTSSP-cross-linked DNA-DOX NGs exhibited higher cytotoxicity than those of free DOX and genipin-cross-linked counterparts except for BEAS-2B cells. It is noted that DNA-DOX NGs exerted greater cytotoxicity toward cancer cells at lower concentrations. The $IC_{50}$ values of DNA-DOX NGs ranged from 1.0 to 2.7 μg/mL, which were significantly lower than those of free DOX (2.9 to 18.9 μg/mL) against the same cell, as shown in Table 2.

TABLE 2

$IC_{50}$ values of free DOX and DNA-DOX NGs on
viability of cancer and non-cancer cells

| Sample | $IC_{50}$ (μg/mL) | | | |
|--------|---------|------|-------|-----|
| | BEAS-2B | A549 | H1299 | LL2 |
| Free DOX | 5.11 | 2.92 | 18.9 | 2.33 |
| Genipin-cross-linked DNA-DOX NGs | 2.54 | 2.62 | 2.59 | 1.30 |
| DTSSP-cross-linked DNA-DOX NGs | 2.45 | 2.35 | 2.34 | 1.07 |

DOX is known to intercalate into DNA, causing DNA breaks and interfering with DNA synthesis. The intracellular DOX uptake through DNA-DOX NGs was investigated to elucidate the cytotoxicity exerted by DNA-DOX NGs against cancer cells. In cell uptake assay, the higher intensity of the red fluorescence in cells indicates the higher intracellular concentration of DOX. FIG. 9 showed a markedly increased red fluorescence in A549 cells observed using a confocal laser scanning microscope. The intracellular fluorescence of DOX in cells increased after treating with DNA-DOX NGs compared to that treated with free DOX.

Flow cytometry results as shown in FIGS. 10A to 10C were in line with above observations. As shown in FIG. 10D, the mean fluorescence intensities in A549, H1299, and LL2 cells treated with DTSSP-cross-linked DNA-DOX NGs were distinctly higher than those treated with free DOX at the same concentration (5.0 μg/mL). This indicated that the DTSSP-cross-linked DNA-DOX NGs enhanced drug uptake in these cells, thus exerting greater cytotoxicity as compared to free DOX (p<0.001).

Additionally, to verify whether DNA-DOX NGs could enhance DOX-induced cytotoxicity, signs of apoptotic molecules were detected. As shown in FIGS. 11A and 11B, the DNA-DOX NGs induced H1299 cells to express higher cleaved caspase-3 and PARP proteins as compared to free DOX after 24 h incubation, suggesting that the DNA-DOX NGs were efficiently delivered into the nuclei to exert cytotoxicity.

Example 6: Characterization of DNA NGs as Vaccine Carriers

The use of DNA NGs as vaccine nanocarriers was evaluated upon loading extracellular secreted protein A (EspA) filament, one of the virulence factors of typical enterohemorrhagic *Escherichia Coli* (EHEC), into the NGs. EHEC is a common cause of bloody diarrhea and hemolytic uremic syndrome and is associated with a higher hazard of death. EspA filament was encapsulated in genipin-crosslinked DNA nanogels (DNA-EspA NGs) following the preparation procedures described above.

Male C57BL/6 mice (7 to 8 weeks) were orally administrated with saline, DNA NGs, EspA or DNA-EspA NGs. Then, their anti-EspA antibodies in serum were measured using the enzyme-linked immunosorbent assay (ELISA) for a total of three times at every other week after vaccination, that is, 14, 28, and 60 days after vaccination. The results were tabulated below in Table 3 and represented by histograms as fold increase in anti-EspA antibody titers in FIG. 12. The histograms representing saline, DNA-NGs and EspA were barely visible because very little fold increases were observed, as shown in Table 3.

TABLE 3

Anti-EspA antibodies measured by ELISA in serum of mice treated with saline, DNA NGs, EspA or DNA-EspA NGs

|  | Saline | DNA NGs | EspA | DNA-EspA NGs |
|---|---|---|---|---|
| 14 days | 0.032 ± 0.004 | 0.975 ± 0.074 | 1.454 ± 0.972 | 605.832 ± 39.342 |
| 28 days | 0.367 ± 0.207 | 1.036 ± 0.215 | 1.436 ± 0.523 | 653.126 ± 132.366 |
| 60 days | 0.055 ± 0.021 | 0.848 ± 0.122 | 1.723 ± 0.598 | 975.539 ± 69.220 |

As shown in Table 3 and FIG. 12, oral vaccinations of DNA-EspA NGs promoted significantly enhanced titers of EspA antibodies in the serum of C57BL/6 mice. On the other hand, the DNA NGs and EspA groups alone could not trigger the production of EspA antibodies. These results suggested that the DNA NGs shell can protect the EspA protein as it passes through the gastrointestinal tract, thereby effectively inducing EspA antibody production.

The foregoing examples are used to exemplify the present disclosure. A person of ordinary skill in the art can conceive the other advantages of the present disclosure, based on the specification of the present disclosure. The present disclosure can also be implemented or applied as described in different examples. It is possible to modify and/or alter the examples for carrying out this disclosure without contravening its spirit and scope for different aspects and applications.

What is claimed is:

1. A composition comprising a plant-derived nucleic acid and a bioactive agent, wherein the plant-derived nucleic acid is crosslinked with a cross-linking agent.

2. The composition of claim 1, wherein the plant-derived nucleic acid is derived from a soft part of a plant.

3. The composition of claim 2, wherein the soft part of the plant is fruits, leaves, petals, flowers, roots, or stems of the plant.

4. The composition of claim 3, wherein the nucleic acid is derived from a seed of the fruit of the plant.

5. The composition of claim 3, wherein the fruit is kiwifruit, dragon fruit, pineapple, papaya, apple, lemon, orange, tangerine, tomato, mango, litchi, pear, date, passion fruit, banana, sweet potato, corn, or a combination thereof.

6. The composition of claim 1, wherein the nucleic acid has a GC content greater than 40%.

7. The composition of claim 1, wherein the cross-linking agent cross-links at least one of primary amines and hydroxyl groups of the nucleic acid.

8. The composition of claim 7, wherein the cross-linking agent is genipin, 3,3'-dithiobis(sulfosuccinimidyl propionate), citric acid, transglutaminase, glutaraldehyde, 1,4-butanediol diglycidyl ether, carbodiimide, tannic acid, sulfonate, oxidized dextrins, hydrazide, alkoxyamine, ketone, periodic acid, calcium chloride, calcium carbonate, or a combination thereof.

9. The composition of claim 1, which has a hydrodynamic diameter of from 50 nm to 5 μm.

10. The composition of claim 9, wherein the hydrodynamic diameter is in a range of from 100 nm to 150 nm.

11. The composition of claim 1, wherein the bioactive agent is hydrophobic.

12. The composition of claim 1, wherein the bioactive agent is an anti-cancer drug, an anti-inflammatory drug, a small molecule compound drug, an anti-virus drug, a vaccine, or a combination thereof.

13. The composition of claim 12, wherein the anti-cancer drug is a chemotherapy drug.

14. The composition of claim 13, wherein the anti-cancer drug is doxorubicin, cisplatin, carboplatin, etoposide, vinorelbine, topotecan, irinotecan, gemcitabine, uracil-tegafur, vinorelbinen, docetaxel, paclitaxel, prednisone, pemetrexed, gefitinib, erlotinib, cetuximab, bevacizumab, or a combination thereof.

15. The composition of claim 12, wherein the anti-virus drug is a nucleic acid analog.

16. The composition of claim 12, wherein the anti-inflammatory drug is selected from the group consisting of zinc oxide, aspirin, ibuprofen, naproxen, meloxicam, celecoxib, and indomethacin.

17. The composition of claim 12, wherein the vaccine is extracellular secreted protein A of enterohemorrhagic *Escherichia coli*, or hemagglutinin and neuraminidase of influenza virus.

18. A method of manufacturing the composition of claim 1 for delivery of the bioactive agent to a subject in need thereof, the method comprising:
  preparing an aqueous phase portion containing the plant-derived nucleic acid and the bioactive agent;

preparing an oil phase portion containing a surfactant;

mixing the aqueous phase portion and the oil phase portion to obtain an emulsified solution;

sonicating the emulsified solution; and removing the oil phase portion so as to obtain the composition from the aqueous phase portion.

* * * * *